(12) United States Patent
Nomura et al.

(10) Patent No.: US 11,002,678 B2
(45) Date of Patent: May 11, 2021

(54) DATA CREATION METHOD AND DATA USE METHOD

(71) Applicant: University of Tsukuba, Tsukuba (JP)

(72) Inventors: Nobuhiko Nomura, Ibaraki (JP); Yutaka Yawata, Ibaraki (JP); Tatsunori Kiyokawa, Ibaraki (JP)

(73) Assignee: University of Tsukuba, Tsukuba (JP)

( * ) Notice: Subject to any disclaimer, the term of this patent is extended or adjusted under 35 U.S.C. 154(b) by 38 days.

(21) Appl. No.: 16/472,727

(22) PCT Filed: Dec. 22, 2017

(86) PCT No.: PCT/JP2017/047414
§ 371 (c)(1),
(2) Date: Jun. 21, 2019

(87) PCT Pub. No.: WO2018/117273
PCT Pub. Date: Jun. 28, 2018

(65) Prior Publication Data
US 2020/0386684 A1    Dec. 10, 2020

(30) Foreign Application Priority Data

Dec. 22, 2016 (JP) .............................. JP2016-249896

(51) Int. Cl.
*G01N 21/64* (2006.01)
*G01N 33/50* (2006.01)

(52) U.S. Cl.
CPC ..... *G01N 21/6458* (2013.01); *G01N 21/6486* (2013.01); *G01N 33/5097* (2013.01);
(Continued)

(58) Field of Classification Search
CPC ........... G01N 21/6458; G01N 21/6486; G01N 33/5097; G01N 2021/6419; G01N 2021/6493
See application file for complete search history.

(56) References Cited

U.S. PATENT DOCUMENTS

| 2003/0082516 A1 | 5/2003 | Straus |
| 2003/0143580 A1 | 7/2003 | Straus |

(Continued)

FOREIGN PATENT DOCUMENTS

| EP | 1 705 477 A2 | 9/2006 |
| EP | 2 818 100 A1 | 12/2014 |

(Continued)

OTHER PUBLICATIONS

International Search Report dated Apr. 3, 2018 in PCT/JP2017/047414 filed Dec. 22, 2017.

(Continued)

*Primary Examiner* — Mark R Gaworecki
(74) *Attorney, Agent, or Firm* — Oblon, McClelland, Maier & Neustadt, L.L.P.

(57) ABSTRACT

A data creation method includes: an autofluorescence data generation step of placing a focus of light having a predetermined wavelength at one set of coordinates on a predetermined focal plane, irradiating a sample positioned at the set of coordinates with excitation light containing the light to obtain autofluorescence emitted from the sample, and generating autofluorescence data including intensity data and/or spectrum data of the autofluorescence; a reflected light data generation step of irradiating the set of coordinates on the predetermined focal plane with illumination light to obtain reflected light scattered by the sample, and generating intensity data of the reflected light; and a correspondence data creation step of creating correspondence data associating the autofluorescence data and the reflected light data on the set of coordinates on the predetermined focal plane.

19 Claims, 34 Drawing Sheets

(15 of 34 Drawing Sheet(s) Filed in Color)

(52) U.S. Cl.
CPC ............ *G01N 2021/6419* (2013.01); *G01N 2021/6493* (2013.01)

(56) References Cited

U.S. PATENT DOCUMENTS

| | | |
|---|---|---|
| 2003/0170613 A1 | 9/2003 | Straus |
| 2004/0243318 A1 | 12/2004 | Ogawa et al. |
| 2004/0245350 A1 | 12/2004 | Zeng |
| 2009/0242797 A1 | 10/2009 | Yazdanfar et al. |
| 2009/0315987 A1 | 12/2009 | Straus |
| 2010/0179934 A1 | 7/2010 | Howley et al. |
| 2010/0248281 A1 | 9/2010 | Straus |
| 2011/0017923 A1 | 1/2011 | Kubo et al. |
| 2011/0033847 A1 | 2/2011 | Walsh et al. |
| 2012/0052524 A1 | 3/2012 | Kinooka et al. |
| 2013/0323718 A1 | 12/2013 | Hyman et al. |
| 2014/0335558 A1 | 11/2014 | Hyman et al. |
| 2015/0003713 A1 | 1/2015 | Duann et al. |
| 2015/0051840 A1 | 2/2015 | Vervier et al. |
| 2017/0029864 A1 | 2/2017 | Straus |
| 2017/0236281 A1 | 8/2017 | Dacosta |

FOREIGN PATENT DOCUMENTS

| | | |
|---|---|---|
| JP | 2005-502354 A | 1/2005 |
| JP | 2006-526767 A | 11/2006 |
| JP | 2010-527017 A | 8/2010 |
| JP | 2012-511905 A | 5/2012 |
| JP | 2015-8727 A | 1/2015 |
| JP | 2015-522249 A | 8/2015 |
| JP | 2015-204813 A | 11/2015 |
| JP | 2016-34925 A | 3/2016 |
| WO | WO 03/008634 A1 | 1/2003 |
| WO | WO 2004/106896 A2 | 12/2004 |
| WO | WO 2010/101225 A1 | 9/2010 |
| WO | WO 2016/011534 A1 | 1/2016 |

OTHER PUBLICATIONS

Robert J Palmer Jr, et al., "Modern microscopy in biofilm research: confocal microscopy and other approaches," Current Opinion in Biotechnology, vol. 10, Issue 3, 1999, pp. 263-268.

Yutaka Yawata, et al., "Monitoring biofilm development in a microfluidic device using modified confocal reflection microscopy," Journal of Bioscience and Bioengineering, vol. 110, No. 3, 2010, pp. 377-380.

Masatoshi Yoshimura, et al., "Discrimination of bacterial species by fluorescence fingerprint spectroscopy with PLS-DA," The Annual Meeting of the Spectroscopical Society of Japan, May 2016, 4 Pages (with English language translation).

Extended European Search Report dated Jun. 15, 2020 in corresponding European Patent Application No. 17884719.0, 8 pages.

DATA CREATION METHOD AND DATA USE METHOD

FIELD

The present invention relates to a data creation method for creating data by measuring autofluorescence emitted by a microorganism, for example, and a data use method for using the data.

BACKGROUND

Conventionally, the species of microorganisms have been typically identified by isolating microorganisms from a specimen and culturing them as systematized in Koch's postulates. There have been developed methods for identifying the species of microorganisms by a metagenomic analysis based on next-generation sequencer technology (refer to Patent Literature 1, for example). According to Patent Literature 1, the species of microorganisms present in a specimen can be identified by comparing base sequences determined by a metagenomic analysis and known base sequences of the microorganisms.

Also widely known are methods for identifying the species of microorganisms by detecting autofluorescence emitted by a colony (refer to Patent Literature 2 and 3, for example). According to Patent Literatures 2 and 3, the species of microorganisms can be detected noninvasively. In addition, there have been developed methods for detecting a cell by: irradiating a fluorescence-stained cell with excitation light having different wavelength bands, photographing fluorescence emitted by the cell to obtain a plurality of images based on the excitation light, and using the obtained images (refer to Patent Literature 4, for example).

Recently, to examine the dynamic state of microorganisms, such researches have been carried out that grasp the position and the movement of the microorganisms in a three-dimensional space using a confocal microscope (refer to Non Patent Literatures 1 and 2, for example). These researches have been produced great results in chronologically and three-dimensionally observing a process of forming a complex (biofilm) of extracellular matrix components produced by a microbial community and microorganisms, for example. An idea of applying the method to identification and evaluation of microorganisms based on autofluorescence at the resolution of single-cell, however, has not been reported. Patent Literatures 1 to 4 do not consider identification of microorganisms by grasping the spatial position and the special movement in the three-dimensional space and acquiring positional information on the microorganisms noninvasively.

Furthermore, the patent documents and the non-patent documents above do not describe or suggest an idea of recording both autofluorescence emitted by a sample and reflected light in a manner associated with each other on one set of coordinates in a space.

CITATION LIST

Patent Literature

Patent Literature 1: Japanese Patent Application Laid-open No. 2015-204813
Patent Literature 2: Japanese Translation of PCT International Application Publication No. 2012-511905
Patent Literature 3: Japanese Translation of PCT International Application Publication No. 2005-502354
Patent Literature 4: PCT Publication No. WO 2003/008634

Non Patent Literature

Non Patent Literature 1: R. J. Palmer and C. Sternberg: Curr. Opin. Biotech., 10, 263(1999)
Non Patent Literature 2: Y. Yawata, K. Toda, E. Setoyama, J. Fukuda, H. Suzuki, H. Uchiyama and N. Nomura: J. Biosci. Bioeng., 110, 377(2010)

SUMMARY

Technical Problem

In view of the circumstances described above, it is an object of the present invention to provide a data creation method and a data use method that can analyze a sample non-invasively and acquire spatial positional information on an object.

Solution to Problem

To solve the above-described problem and attain the object, a data creation method according to the present invention includes: an autofluorescence data generation step of placing a focus of excitation light having a predetermined wavelength at one set of coordinates on a predetermined focal plane, irradiating a sample positioned at the set of coordinates with the excitation light to obtain autofluorescence emitted from the sample, and generating autofluorescence data including intensity data and/or spectrum data of the autofluorescence; a reflected light data generation step of irradiating the set of coordinates on the predetermined focal plane with illumination light to obtain reflected light scattered by the sample, and generating intensity data of the reflected light; and a correspondence data creation step of creating correspondence data associating the autofluorescence data and the intensity data of the reflected light on the set of coordinates on the predetermined focal plane.

In the data creation method according to the present invention, the data creation method is performed on a plurality of different sets of coordinates on the predetermined focal plane.

In the data creation method according to the present invention, the data creation method is performed on a plurality of different focal planes.

In the data creation method according to the present invention, the autofluorescence data generation step includes outputting a plurality of rays of excitation light having different wavelengths and creating the autofluorescence data including spectrum profile data containing a plurality of pieces of the spectrum data of the autofluorescence obtained by the respective rays of excitation light.

In the data creation method according to the present invention, the reflected light data generation step includes obtaining the reflected light using any one of the rays of excitation light having different wavelengths.

In the data creation method according to the present invention, the reflected light data generation step includes obtaining the reflected light using all the rays of excitation light having different wavelengths.

In the data creation method according to the present invention, the autofluorescence data generation step is performed only on a set of coordinates from which the reflected light having an intensity equal to or higher than a predetermined intensity is obtained at the reflected light data generation step.

In the data creation method according to the present invention, the autofluorescence data generation step is performed on a plurality of sets of coordinates from which the reflected light having an intensity equal to or higher than a predetermined intensity is obtained at the reflected light data generation step and on one or a plurality of sets of coordinates positioned in a region that is surrounded by the sets of coordinates and that corresponds to an inside of the sample.

In the data creation method according to the present invention, at least one of the excitation light and the illumination light is laser light.

A data use method according to the present invention includes generating the correspondence data by the data creation method according to the present invention and finding out correlation with a state of a sample by comparing a plurality of pieces of the autofluorescence data of the sample.

In the data use method according to the present invention, the correlation is found out by machine learning.

A data use method according to the present invention includes generating the correspondence data by the data creation method according to the present invention and identifying or evaluating an unknown sample by comparing the autofluorescence data of a known sample with the autofluorescence data of the unknown sample.

In the data use method according to the present invention, the known sample is characterized by machine learning.

In the data use method according to the present invention, the sample is any one of an animal cell, a plant cell, an yeast cell, an eumycetes cell, a microalgae cell, a bacterium, an archaeon, a virus, and a phage and any one of a spore, a sporule, and a membrane vesicle produced by the cells and the organisms.

In the data use method according to the present invention, the state of the sample relates to a metabolic state or a physiological state of the sample.

In the data use method according to the present invention, identification of the unknown sample is to identify a biological kingdom, phylum, class, order, family, genus, species, breed, pathotype or serotype.

In the data use method according to the present invention, identification of the unknown sample is to identify a microbiological strain or sub-strain.

In the data use method according to the present invention, evaluation of the unknown sample relates to a metabolic state or a physiological state.

A data use method according to the present invention includes: an autofluorescence data generation step of placing a focus of light having a predetermined wavelength at one set of coordinates on a predetermined focal plane, irradiating a sample positioned at the set of coordinates with excitation light containing the light to obtain autofluorescence emitted from the sample, and generating autofluorescence data including intensity data and/or spectrum data of the autofluorescence; a reflected light data generation step of irradiating the set of coordinates on the predetermined focal plane with illumination light to obtain reflected light scattered by the sample, and generating intensity data of the reflected light; a correspondence data creation step of creating correspondence data associating the autofluorescence data and the intensity data of the reflected light on the set of coordinates on the predetermined focal plane; a repetition step of repeating the autofluorescence data generation step, the reflected light data generation step, and the correspondence data creation step on a plurality of different focal planes; and an extraction step of extracting a group having a predetermined property using the correspondence data obtained by the repetition step. Advantageous Effects of Invention The present invention can analyze a sample non-invasively and acquire spatial positional information on an object.

BRIEF DESCRIPTION OF DRAWINGS

FIG. 17 is a view of a three-dimensional image obtained by coloring *S. mitis* and A.a.

DESCRIPTION OF EMBODIMENTS

Exemplary aspects (hereinafter, referred to as "embodiments") to embody the present invention are described below with reference to the accompanying drawings.

Embodiments

Figure 1:
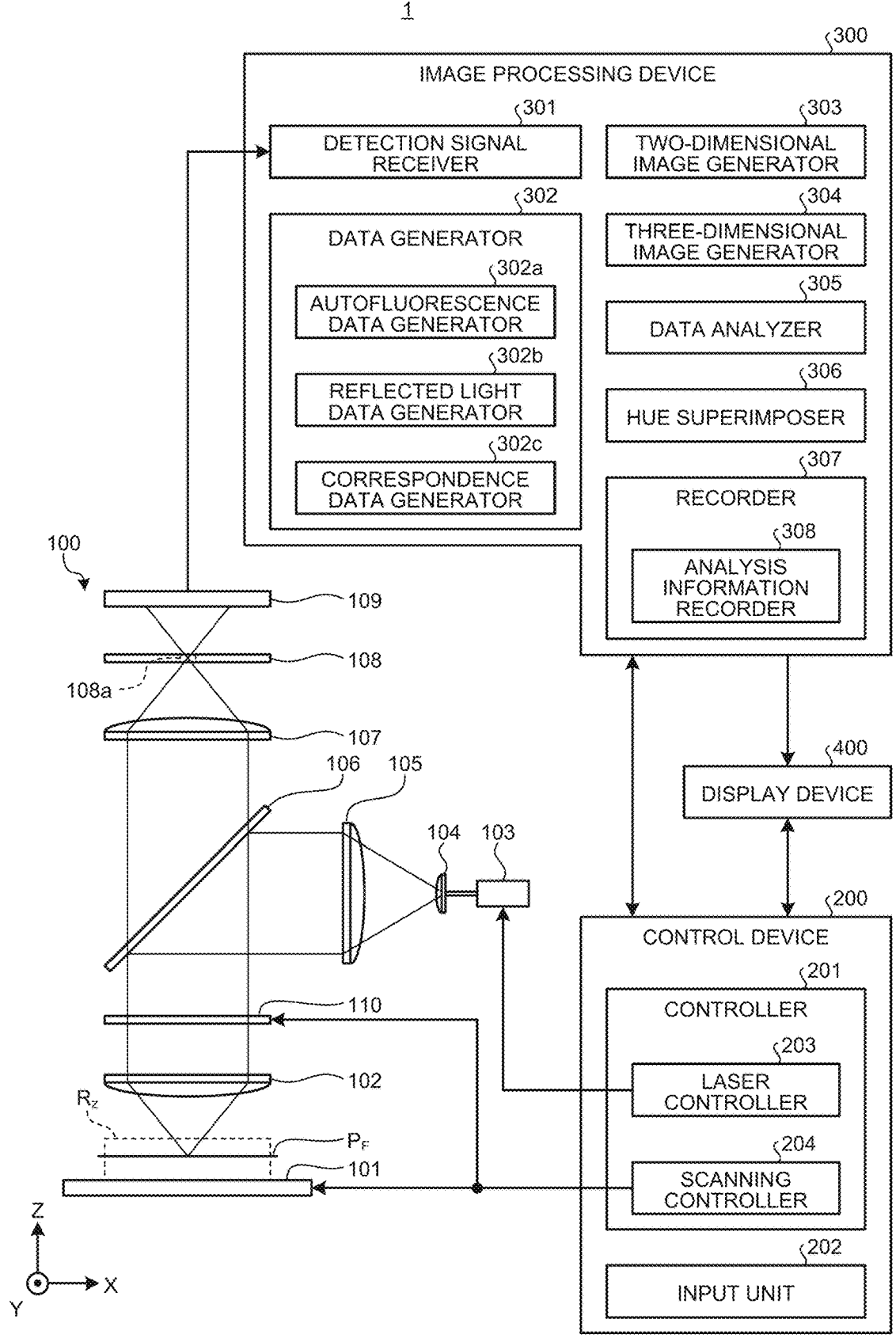
FIG. 1 is a schematic of a configuration of a microscopic system according to an embodiment of the present invention.

FIG. 1 is a schematic of a configuration of a microscopic system according to an embodiment of the present invention. A microscopic system 1 illustrated in FIG. 1 identifies the kind of an object included in an image, such as the species of a microorganism, based on image data obtained by a confocal laser scanning microscope 100 and displays the identification results and the obtained image. As illustrated in FIG. 1, the microscopic system 1 includes the confocal laser scanning microscope 100, a control device 200, an image processing device 300, and a display device 400. The confocal laser scanning microscope 100 irradiates a specimen with laser light and obtains autofluorescence emitted by the specimen or reflected light. The control device 200 collectively controls the microscopic system 1. The image processing device 300 generates various kinds of data, such as image data, based on the light obtained by the confocal laser scanning microscope 100. The display device 400 displays an image based on the display image data generated by the image processing device 300. Examples of the microorganisms include, but are not limited to, bacteria, fungi, viruses, microalgae, protozoans, etc. A sample to be photographed according to the present embodiment is any one of animal cells, plant cells, yeast cells, eumycetes cells, microalgae cells, bacteria, archaea, viruses, and phages and any one of spores, sporules, and membrane vesicles produced by these cells and organisms.

The confocal laser scanning microscope 100 includes a stage 101, an object lens 102, a laser light source 103, a lens 104, a collimating lens 105, a beam splitter 106, an imaging lens 107, a confocal pinhole 108, a detector 109, and a scanning mirror 110. In the following description, an X-axis and a Y-axis are two axes orthogonal to a plane parallel to a specimen placing surface of the stage 101, and a Z-direction is an axis orthogonal to the plane. The Z-axis is parallel to an optical axis of the object lens 102.

The stage 101 is a plate on which a specimen is placed. The stage 101 can be moved in the Z-axis direction using a driving source, such as a motor, under the control by the control device 200. The specimen is a solution or a medium including a microorganism and is placed on the stage 101 in a manner held by a holding member, such as a Petri dish and a microscope slide.

The object lens 102 gathers laser light reflected by the beam splitter 106 toward the stage 101. In addition, the object lens 102 makes light from the specimen on the stage 101 into parallel light and causes the light to enter into the beam splitter 106.

The laser light source 103 outputs laser light having a predetermined wavelength. Specifically, the laser light source 103 outputs laser light having a wavelength corresponding to an excitation wavelength for exciting the specimen. The laser light source 103 may include a plurality of light sources that can output laser light having different wavelengths to be used. Alternatively, the laser light source 103 may output white laser light and select the wavelength of light to be output by a filter.

The lens 104 outputs the laser light output from the laser light source 103 as radial laser light.

The collimating lens 105 makes the radial laser light that has passed through the lens 104 into parallel light and outputs the light to the beam splitter 106.

The beam splitter 106 allows part of entering light to pass therethrough and reflects the other part of the light. Specifically, the beam splitter 106 bends part of the light output from the laser light source 103 toward the object lens 102. In addition, the beam splitter 106 allows part of the light entering from the object lens 102 to pass therethrough and causes the light to enter into the imaging lens 107. The beam splitter 106 is provided as a half mirror, for example, and reflects half of the entering laser light and reflects the other half of the laser light.

The imaging lens 107 focuses the light that has passed through the beam splitter 106.

The confocal pinhole 108 allows at least part of the light focused by the imaging lens 107 to pass therethrough. The confocal pinhole 108 has a pinhole 108a serving as a hole through which light can pass. The confocal pinhole 108 and the object lens 102 are provided at conjugate positions. In the confocal pinhole 108, light from a focal plane of the object lens 102 passes through the pinhole 108a, and light from an out-of-focus position is blocked. If the spot diameter of the laser light focused by the imaging lens 107 is 0.2 µm, for example, light from a range of approximately 0.03 µm$^2$ passes through the pinhole 108a. The diameter of the pinhole 108a and the size of the focal space can be changed.

The detector 109 is provided as a reflective diffraction grating and a plurality of photomultiplier tubes (PMTS, which may be hereinafter referred to as channels). The reflective diffraction grating separates entering light into light having specified wavelength bands. The PMT performs photoelectric conversion on the obtained light and amplifies the electric current of electrical signals resulting from conversion. The detector 109, for example, separates the entering light into 32 rays of light having different wavelength bands, and the 32 rays of light resulting from separation enter into respective 32 PMTs. The PMTs each perform photoelectric conversion on the entering light and output the electrical signals.

The scanning mirror 110 controls a laser light irradiation position on a focal plane $P_F$ of the specimen under the control by the control device 200. The scanning mirror 110 is provided as an X-position control mirror and a Y-position control mirror, for example, and guides the laser light to a predetermined position on the X-Y plane.

The scanning mirror 110 moves the laser light irradiation position along a scanning path set in advance by changing the angle of the position control mirrors under the control by the control device 200.

The following describes the configuration of the control device 200. The control device 200 includes a controller 201 and an input unit 202. The control device 200 also includes a recorder (not illustrated) that records therein various kinds of information required for the operations of the control device 200.

The controller 201 is provided as a central processing unit (CPU) and various kinds of arithmetic circuits having arithmetic and control functions. The controller 201 collectively controls the microscopic system 1 by reading the information stored in the recorder and performing various kinds of arithmetic processing. The controller 201 includes a laser controller 203 and a scanning controller 204.

The laser controller 203 controls output of the laser light by the laser light source 103 based on a control program and instruction information received by the input unit 202. Specifically, the laser controller 203 controls the output timing of the laser light and the wavelength of the laser light to be output. The laser controller 203 performs control to output the laser light intermittently by pulse control, for example.

The scanning controller 204 controls the position of the stage 101 in the Z-direction and the laser light irradiation position by the scanning mirror 110 based on a control program and instruction information received by the input unit 202.

The input unit 202 receives input of various kinds of information. The input unit 202 is provided as a user interface, such as a keyboard, a mouse, and a touch panel.

The following describes the configuration of the image processing device 300. The image processing device 300 includes a detection signal receiver 301, a data generator 302, a two-dimensional image generator 303, a three-dimensional image generator 304, a data analyzer 305, a hue superimposer 306, and a recorder 307.

The detection signal receiver 301 receives electrical signals of respective channels from the detector 109. The detection signal receiver 301 outputs the received electrical signals of the respective channels and positional information (laser light irradiation position) on the scanning plane in a manner associated with each other to the data generator 302.

The detection signal receiver 301 may include a part for detecting reflected light and a part for detecting autofluorescence separately.

The data generator 302 generates data associating the intensity of light based on the electrical signals received from the detection signal receiver 301 with the positional information on the scanning plane. The data generator 302 includes an autofluorescence data generator 302a, a reflected light data generator 302b, and a correspondence data generator 302c.

The autofluorescence data generator 302a acquires the electrical signals relating to autofluorescence received by the detection signal receiver 301, that is, the electrical signals of the respective channels and generates intensity data and/or a fluorescence spectrum (spectrum data) for each set of coordinates on a predetermined focal plane. If one ray of excitation light is output to one position on the scanning plane, the autofluorescence data generator 302a generates one fluorescence spectrum. If rays of excitation light having different wavelengths are output at different timings, the autofluorescence data generator 302a generates a plurality of fluorescence spectra corresponding to the rays of excitation light. The "fluorescence spectrum" means "intensity distribution to the wavelength" of autofluorescence generated when the laser light having a predetermined wavelength is output as the excitation light. The "intensity" indicates a signal value resulting from photoelectric conversion on the obtained autofluorescence, for example. The fluorescence spectrum has a wave form resulting from smoothing by interpolation between plots, for example. In the present invention, data consisting of a plurality of fluorescence spectra may be referred to as spectrum profile data. In the present specification, "autofluorescence data" includes any one or all of the intensity data, the spectrum data, and the spectrum profile data of autofluorescence. The autofluorescence data generator 302a generates the autofluorescence data indicating the fluorescence spectrum generated based on the excitation wavelength for each of positions (a plurality of sets of coordinates on the predetermined focal plane) on the scanning plane.

The reflected light data generator 302b acquires the detection signals received by the detection signal receiver 301 and relating to reflected light reflected by the specimen and generates reflected light data associating the intensity of reflected light based on the acquired detection signals with the positional information on the scanning plane. The reflected light data generator 302b adds up the intensities of light based on the electrical signals of the channels, for example, and determines the intensity resulting from addition to be the intensity of the reflected light at a position on the scanning plane.

The correspondence data generator 302c generates correspondence data consisting of the autofluorescence data and the reflected light data at one set of coordinates on the predetermined focal plane. If the autofluorescence data and the reflected light data are generated at a plurality of sets of coordinates, the correspondence data generator 302c generates the correspondence data associating the autofluorescence data with the reflected light data for each set of coordinates. If a plurality of pieces of autofluorescence data due to a plurality of rays of excitation light are generated at a single set of coordinates, the correspondence data generator 302c associates the pieces of autofluorescence data with the set of coordinates.

The following describes the significance of associating the reflected light data with the autofluorescence data on one set of coordinates on the predetermined focal plane. The intensity of reflected light depends on the presence of a specimen, such as a cell, at one set of coordinates on the predetermined focal plane. If no specimen (cell) is present at the set of coordinates, the intensity of reflected light is low. If a specimen (cell) is present, reflected light having a high intensity can be obtained. By obtaining reflected light at high magnification, the microscopic system 1 can obtain reflected light from the outline of a cell, from the inside of the cell, and from an intracellular organelle, such as a nucleus, inside the cell. As described above, the microscopic system 1 acquires information on whether a specimen (cell) is present at a certain set of coordinates or which region of the specimen (cell) the certain set of coordinates correspond to. By using the information and the autofluorescence data at the set of coordinates, the microscopic system 1 can perform identification or evaluation on a cellular level or an intracellular organellar level, which has been impossible to perform.

The two-dimensional image generator 303 generates two-dimensional image data corresponding to a display image of one frame based on the various kinds of data generated by the data generator 302. In generating focused image data based on reflected light, for example, the two-dimensional image generator 303 generates one piece or a plurality of pieces of focused image data corresponding to the number of scanned scanning planes based on the reflected light data generated by the reflected light data generator 302b. The focused image data is supplied with luminance information on each pixel position. In generating fluorescence image data based on autofluorescence generated by output excitation light, the two-dimensional image generator 303 generates one piece or a plurality of pieces of fluorescence image data corresponding to the number of scanned scanning planes based on the florescence spectrum out of the correspondence data generated by the correspondence data generator 302c and on results of an analysis by the data analyzer 305. The fluorescence image data is supplied with the luminance information on each pixel position. The two-dimensional image generator 303 performs image processing using publicly known techniques, such as gain processing, contrast processing, and gamma correction, on the generated two-dimensional image data of one frame. In addition, the two-dimensional image generator 303 generates a display image data by performing processing corresponding to the display specification of the display device 400. The focused image based on reflected light may be hereinafter referred to as a confocal reflection microscopy (CRM) image.

The three-dimensional image generator 304 generates three-dimensional image data based on the two-dimensional image data generated by the two-dimensional image generator 303. The three-dimensional image generator 304 generates the three-dimensional image data by supplying the luminance information on each frame to the three-dimensional space.

The laser light irradiation position is associated with spatial information on the image data generated by the two-dimensional image generator 303 and the three-dimensional image generator 304. A two-dimensional spatial position is positional information indicating a position (X-position) of a pixel on the X-axis and a position (Y-position) of the pixel on the Y-axis. A three-dimensional spatial position is positional information indicating an X-position, a Y-position, and a position (Z-position) of the pixel on the Z-axis. The scanning plane corresponds to a plane orthogonal to the Z-axis, for example. A position on the scanning plane is represented by an X-position and a Y-position on the scanning plane.

The data analyzer 305 analyzes various kinds of data relating to the specimen using the correspondence data generated by the data generator 302. The data analyzer 305, for example, identifies the kind of a specimen, evaluates the state, and extracts a specimen having predetermined properties. Specifically, in identifying a specimen, the data analyzer 305 refers to an identification table recorded in the recorder 307 to determine whether there is a kind having a spectrum pattern matching with the fluorescence spectrum associated with the position to be analyzed. The data analyzer 305 generates identification information associating the laser light irradiation position with the identified kind.

The hue superimposer 306 superimposes a specified hue on a corresponding pixel position in the image based on the identification information generated by the data analyzer 305. Specifically, if the image to be displayed is a three-dimensional image, and the species of a microorganism to be colored in red is specified, the hue superimposer 306 performs processing of applying red to the pixel position determined to be the corresponding species of a microorganism. The hue superimposer 306 outputs superimposition image data on which the hue is superimposed to the display device 400. The superimposition image data is obtained by supplying information on the hue to the two-dimensional image data or the three-dimensional image data.

The recorder 307 records therein various kinds of computer programs including a computer program for performing the operations of the image processing device 300. The recorder 307 is provided as a read only memory (ROM) in which the various kinds of computer programs or the like are installed in advance and a random access memory (RAM) that records therein arithmetic parameters, for example.

The recorder 307 includes an analysis information recorder 308 that records therein data required for an analysis, such as the identification table used to identify the kinds by the data analyzer 305. If the identification table is a table used to identify the kinds (species) of microorganisms, for example, the species of microorganisms are associated with respective spectrum patterns including one or a plurality of fluorescence spectra characterized by each excitation wavelength. The data is not limited to the identification table and may have such a data form that can output the information corresponding to the input information. The analysis information recorder 308 may record therein analysis results, such as the identification information generated by the data analyzer 305.

The display device 400 is provided as a liquid crystal or organic electroluminescence (EL) display and displays an image or the like generated by the image processing device 300. The display device 400 may display various kinds of information generated by the control device 200.

Figure 2:
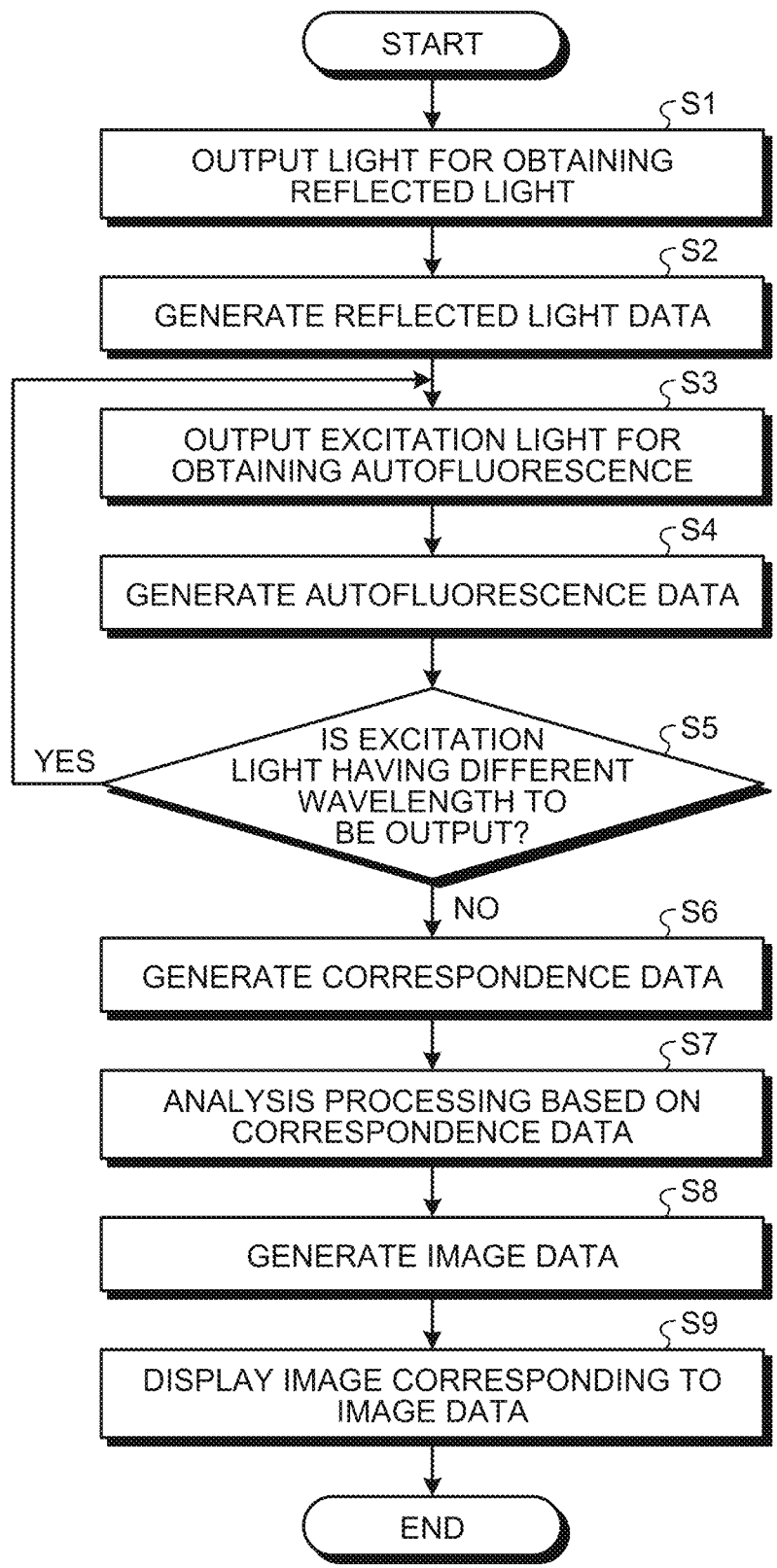
FIG. 2 is an exemplary flowchart for explaining a data analysis method for analyzing data according to the embodiment of the present invention.

The following describes a data analysis method by the microscopic system 1 with reference to FIG. 2. FIG. 2 is an exemplary flowchart for explaining the data analysis method according to the embodiment of the present invention. The following describes a process of analyzing a specimen and generating the superimposition image data based on the obtained autofluorescence.

In the data analysis method according to the present embodiment, the microscopic system 1 irradiates a specimen with light having a wavelength or a wavelength band set in advance to obtain reflected light under the control by the controller 201 (Step S1). The detection signal receiver 301 acquires detection signals corresponding to autofluorescence generated by the light or to reflected light reflected by the specimen. The present embodiment obtains the autofluorescence or the reflected light by three-dimensionally scanning a focal position of laser light for obtaining reflected light to generate data in the three-dimensional space.

Figure 3:
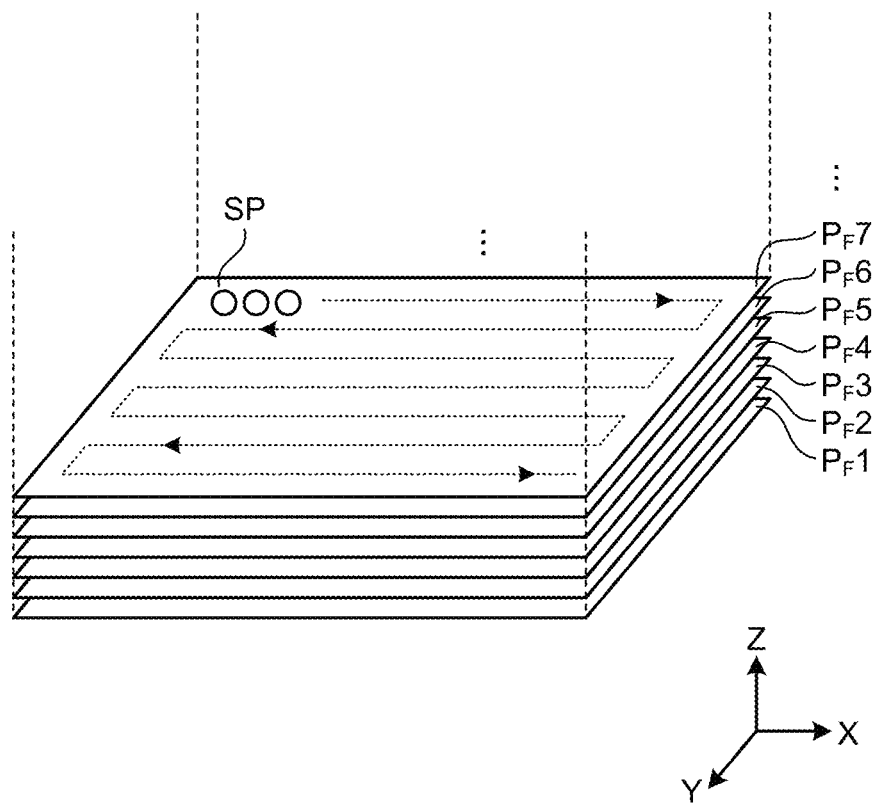
FIG. 3 is a schematic for explaining a scanning method by the microscopic system according to the embodiment of the present invention.

The following describes a scanning method performed by the microscopic system 1 with reference to FIG. 3. FIG. 3 is a schematic for explaining the scanning method by the microscopic system according to the embodiment of the present invention. After scanning the X-Y plane on a focal plane at a certain Z-position and receiving light from the specimen, the confocal laser scanning microscope 100 changes the Z-position and scans the X-Y plane at the changed Z-position. The confocal laser scanning microscope 100, for example, performs scanning at each of Z-positions specified in a Z-scanning range $R_Z$ illustrated in FIG. 1, thereby obtaining light (reflected light or autofluorescence) from a plurality of positions on the focal plane at the respective Z-positions. In the confocal laser scanning microscopic 100, the configurations of the beam splitter 106 and the detector 109 can be appropriately changed depending on the image to be generated.

As illustrated in FIG. 3, for example, the confocal laser scanning microscope 100 performs scanning with laser light on a focal plane $P_F1$ and then moves the stage 101 in the Z-axis direction. Subsequently, the confocal laser scanning microscope 100 performs scanning with laser light on a focal plane $P_F2$ where the focus of the laser light is positioned after the movement. Similarly, the confocal laser scanning microscope 100 sequentially performs scanning on focal planes $P_F3$, $P_F4$, $P_F5$, $P_F6$, and $P_F7$ in the Z-scanning range $R_Z$ set in advance.

In the scanning method on the X-Y plane, the confocal laser scanning microscope 100 outputs laser light from one of the corners of a rectangular focal plane (focal plane $P_F7$ in FIG. 3) and receives light from a spot SP serving as an irradiation region as illustrated in FIG. 3, for example. By scanning the spot SP in a zigzag manner, the confocal laser scanning microscope 100 can obtain light corresponding to the number of pieces of data required to generate one two-dimensional image (focused image) on the focal plane $P_F7$. By making the diameter of the spot SP substantially equal to the size of one pixel (corresponding to one dot displayed on a monitor), for example, the confocal laser scanning microscope 100 can represent the colors of the two-dimensional image and the three-dimensional image in units of pixels. In addition, the confocal laser scanning microscope 100 can color visual information corresponding to the identification information in units of pixels. Being "substantially equal to the size of one pixel" indicates that, if the spot SP is a circle, the spot SP has substantially the same size as that of an incircle of the pixel. The scanning path described above is given by way of example only, and it is not limited thereto if the confocal laser scanning microscope 100 can scan the focal plane. The diameter of the spot SP has a lower limit of approximately 0.2 μm, which is the limit of resolution of the optical microscope, and can be approximately adjusted by changing the diameter of the confocal pinhole.

At Step S2 subsequent to Step S1, the reflected light data generator 302b acquires detection signals relating to the reflected light received by the detection signal receiver 301 and generates reflected light data based on the acquired detection signals (reflected light data generation step).

At Step S3 subsequent to Step S2, the microscopic system 1 irradiates the specimen with light (excitation light) having a wavelength or a wavelength band set in advance to obtain autofluorescence under the control by the controller 201. In the present flowchart, the excitation light for obtaining autofluorescence and irradiation light (e.g., excitation light having the same wavelength) for obtaining reflected light are output at different timings to obtain the light. Alternatively, the microscopic system 1 may irradiate the sample with excitation light only once and obtain autofluorescence and reflected light by making respective detection times different.

Subsequently, the autofluorescence data generator 302a acquires detection signals relating to the autofluorescence received by the detection signal receiver 301 and generates autofluorescence data based on the acquired detection signals (Step S4: autofluorescence data generation step). The autofluorescence data includes a fluorescence spectrum of the autofluorescence generated by the excitation light output to the specimen at Step S1.

In the data generation at Steps S1 and S2 and Steps S3 and S4, the processing at Steps S3 and S4 may be performed first or performed in parallel with the processing at Steps S1 and S2.

At Step S5 subsequent to Step S4, the controller 201 determines whether to output excitation light having a wavelength (or wavelength band) different from the wavelength (or wavelength band) of the excitation light for obtaining autofluorescence output at Step S3. The controller 201 refers to scanning conditions set in advance or scanning conditions specified through the input unit 202 to determine whether another excitation light to be output is present.

At Steps S2 and S4, the microscopic system 1 generates the fluorescence spectrum of autofluorescence or the intensity of reflected light obtained when laser light having a certain excitation wavelength is output to one point on a certain z-position on the focal plane. If a plurality of excitation wavelengths are set in advance, the microscopic system 1 repeats scanning with laser light having the excitation wavelengths, thereby generating fluorescence spectra having different excitation wavelengths at the same position. By repeating the scanning as described above, the microscopic system 1 generates fluorescence spectra corresponding to the excitation wavelengths at respective positions on a plurality of focal planes. The "focal plane" herein indicates a plane orthogonal to the optical axis of the laser light and on which the focus of the laser light is positioned.

If the controller 201 determines that excitation light having a wavelength different from that of the light output at Step S3 needs to be output (Yes at Step S5), the microscopic system 1 performs the processing at Step S3 again to repeat scanning using the specified excitation light. If the controller 201 determines that another excitation light need not be output (No at Step S5), the microscopic system 1 performs the processing at Step S6.

At Step S6, the correspondence data generator 302c generates correspondence data associating the intensity of reflected light generated at Step S2 with the fluorescence spectrum generated at Step S3 (correspondence data creation step). If a plurality of fluorescence spectra are generated by irradiation of a plurality of rays of excitation light, the fluorescence spectra are associated with the intensity of reflected light for one laser light irradiation position. The intensity of reflected light may be the total of the intensities of reflected light obtained by all the rays of excitation light having different wavelengths (or wavelength bands) for one laser light irradiation position. Alternatively, the intensity of reflected light may be the intensity of reflected light obtained by the excitation light having a wavelength set in advance.

At Step S7 subsequent to Step S6, the data analyzer 305 performs analysis processing on the specimen based on the correspondence data generated at Step S5. The data analyzer 305 according to the present embodiment identifies the kind of a microorganism at each of the spot positions. A specific example of the analysis processing will be described later.

At Step S8 subsequent to Step S7, the two-dimensional image generator 303, the three-dimensional image generator 304, and the hue superimposer 306 generate image data based on the correspondence data. At Step S8, the two-dimensional image generator 303 generates a plurality of pieces of focused image data first using the reflected light data in the correspondence data.

Figure 4:
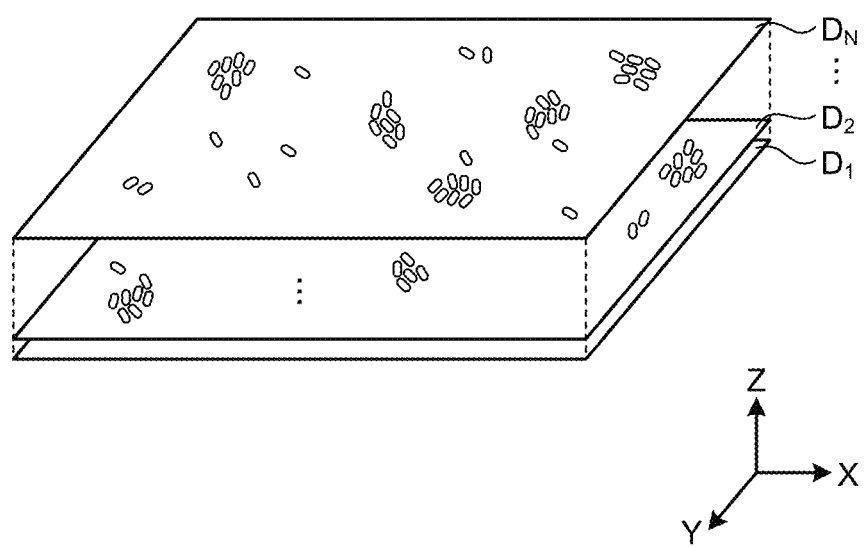
FIG. 4 is a schematic for explaining a focused image generated by scanning by the microscopic system according to the embodiment of the present invention.

FIG. 4 is a schematic for explaining a focused image generated by scanning by the microscopic system according to the embodiment of the present invention. The two-dimensional image generator 303 performs image processing based on the intensity of reflected light in the correspondence data generated by the correspondence data generator 302c. As a result, N focused images $D_1, D_2, \ldots,$ and $D_N$ are obtained (N is a natural number of 3 or larger) based on the light reflected on the respective focal planes as illustrated in FIG. 4. The two-dimensional image generator 303 converts the intensity of reflected light obtained at the respective positions into luminance information and generates a plurality of pieces of focused image data arrayed corresponding to the laser light irradiation positions. In other words, the two-dimensional image generator 303 generates two-dimensional image data including the image generated by the reflected light and the positional information (e.g., the Z-position) relating to the laser light irradiation position.

If the pieces of focused image data (focused images $D_1, D_2, \ldots,$ and $D_N$) are generated, the three-dimensional image generator 304 associates the luminance information on the focused images with a Cartesian coordinate system in a three-dimensional space. The three-dimensional image generator 304 thus generates three-dimensional image data representing a specimen image corresponding to the luminance on the three-dimensional space.

Figure 5:
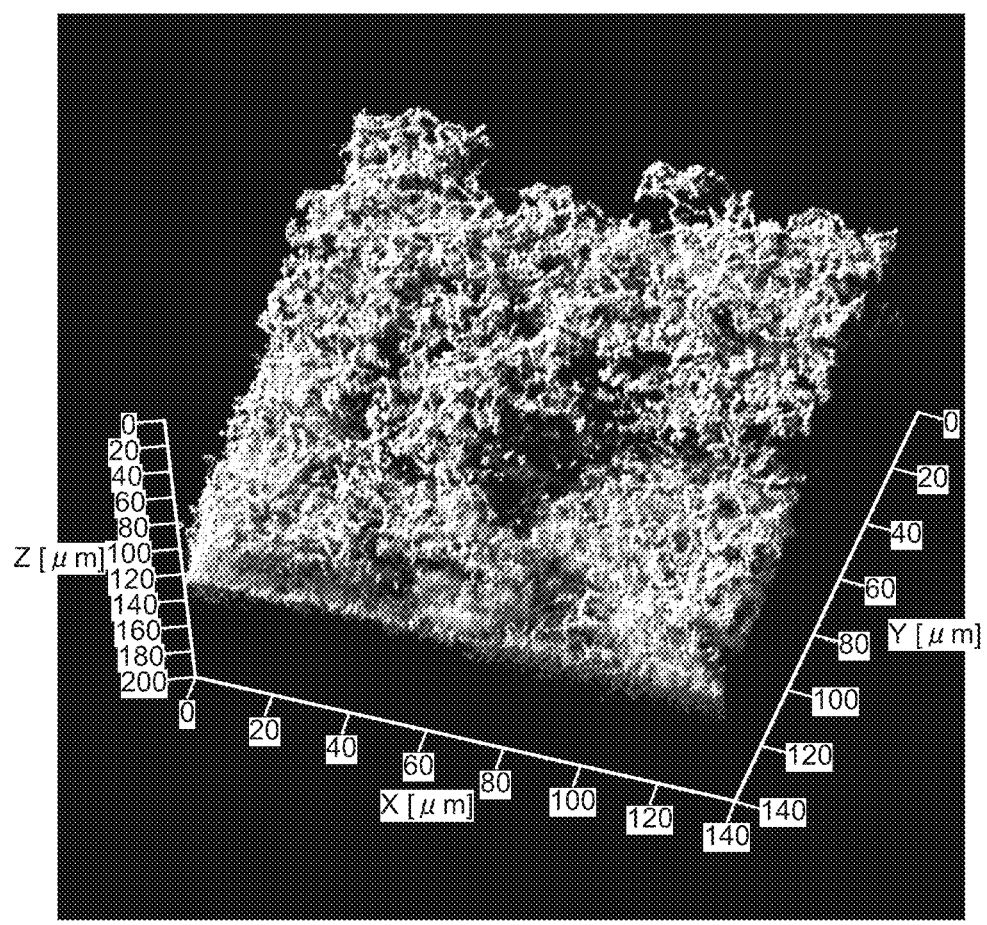
FIG. 5 is a view for explaining a three-dimensional image displayed by the microscopic system according to the embodiment of the present invention.

FIG. 5 is a view for explaining a three-dimensional image displayed by the microscopic system according to the embodiment of the present invention. The three-dimensional image generator 304 generates three-dimensional image data including a three-dimensional image consisting of a set of points of brightness corresponding to the luminance as illustrated in FIG. 5. While FIG. 5 illustrates a grayscale three-dimensional image having shades varying depending on the luminance, the conditions of hues and the like can be appropriately changed.

After the three-dimensional image data is generated, the hue superimposer 306 selects hues to be superimposed on respective positions (positions on the two-dimensional space or the three-dimensional space) based on the identification information generated by the data analyzer 305 and the conditions set in advance. The hue superimposer 306 thus generates superimposition image data by superimposing the hues on the three-dimensional image data generated by the three-dimensional image generator 304. Let us assume a case where microorganisms of *Streptococcus mitis* (*S. mitis*) and Aggregatibacter actinomycetemcomitans (A.a.) are present in the specimen, and conditions that *S. mitis* is colored in red and that A.a is colored in green are set, for example. In this case, the hue superimposer 306 performs processing of coloring the position (pixel position) in the image corresponding to the laser light irradiation position identified as *S. mitis* in red and coloring the position in the image corresponding to the laser light irradiation position identified as A.a. in green.

At Step S9 subsequent to Step S8, the image processing device 300 causes the display device 400 to display the superimposition image data generated by the hue superimposer 306 under the control by the control device 200. By the processing described above, the display device 400 displays a superimposition image obtained by coloring the specimen image generated by irradiation of the excitation light based on the analysis results (kinds).

The following describes the analysis processing at Step S7 with reference to the drawings. In the analysis processing at Step S7, the data analyzer 305 identifies a biological kingdom, phylum, class, order, family, genus, species, breed, pathotype or serotype, identifies a microbiological strain or sub-strain, and evaluates the state of a sample relating to the metabolic state or the physiological state of an unknown sample or a known sample based on the processing contents. The following describes an example of the analysis processing at Step S7 with reference to FIGS. 6 to 19. Fluorescence spectra based on autofluorescence are described first with reference to FIGS. 6 to 13B. The following description uses images and fluorescence spectra of *S. mitis* and A.a as examples.

Figure 6:
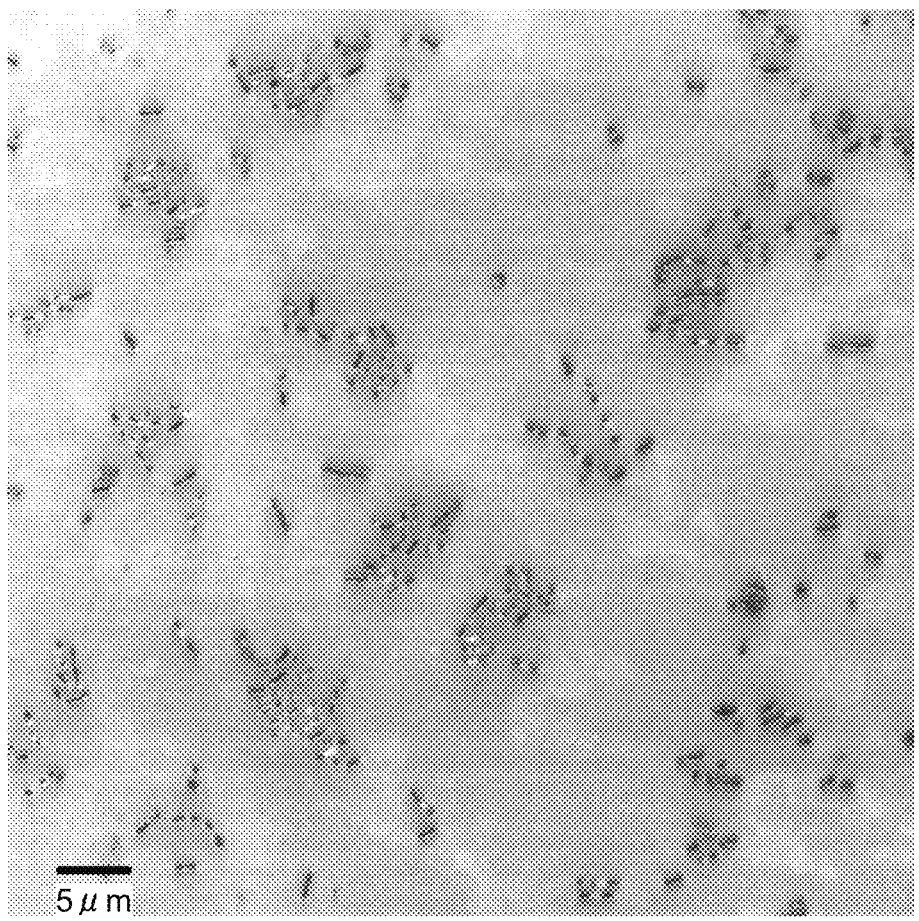
FIG. 6 is a view of a specimen image including *Streptococcus mitis* (*S. mitis*) serving as an example of an object to be identified by the microscopic system according to the embodiment of the present invention.

FIG. 6 is a view of a specimen image including *S. mitis* serving as an example of an object to be identified by the microscopic system according to the embodiment of the present invention. A scale is displayed at the lower left in the figure. FIG. 6 illustrates a focused image obtained by outputting laser light having a wavelength or a wavelength band set in advance. By displaying the focused image as illustrated in FIG. 6, the two-dimensional positions of microorganisms (*S. mitis* in this example) can be visually recognized.

Figure 7A:
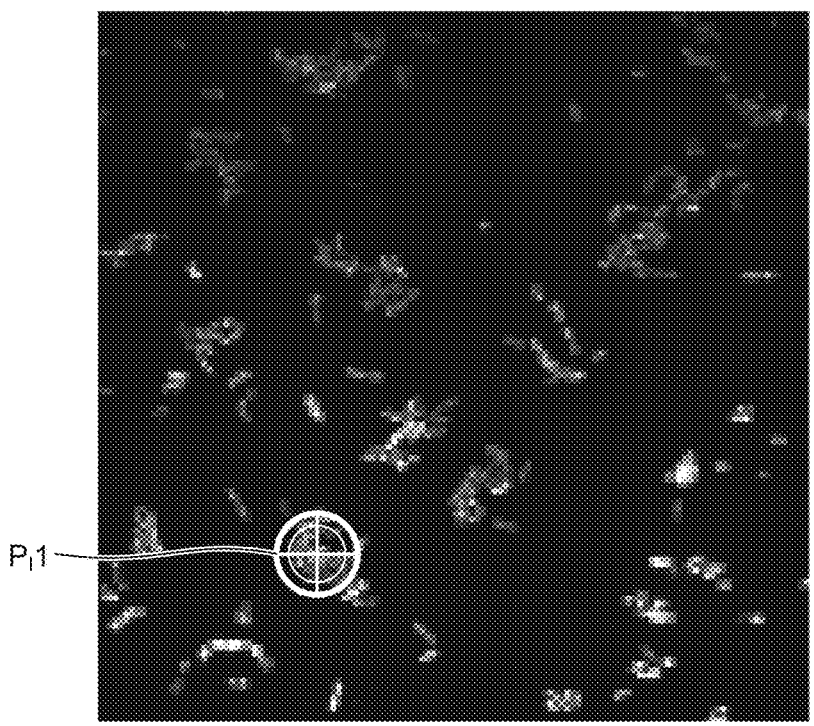
FIG. 7A is a view of a fluorescence image of *S. mitis* photographed when being irradiated with excitation light having a wavelength of 405 nm.
Figure 7B:
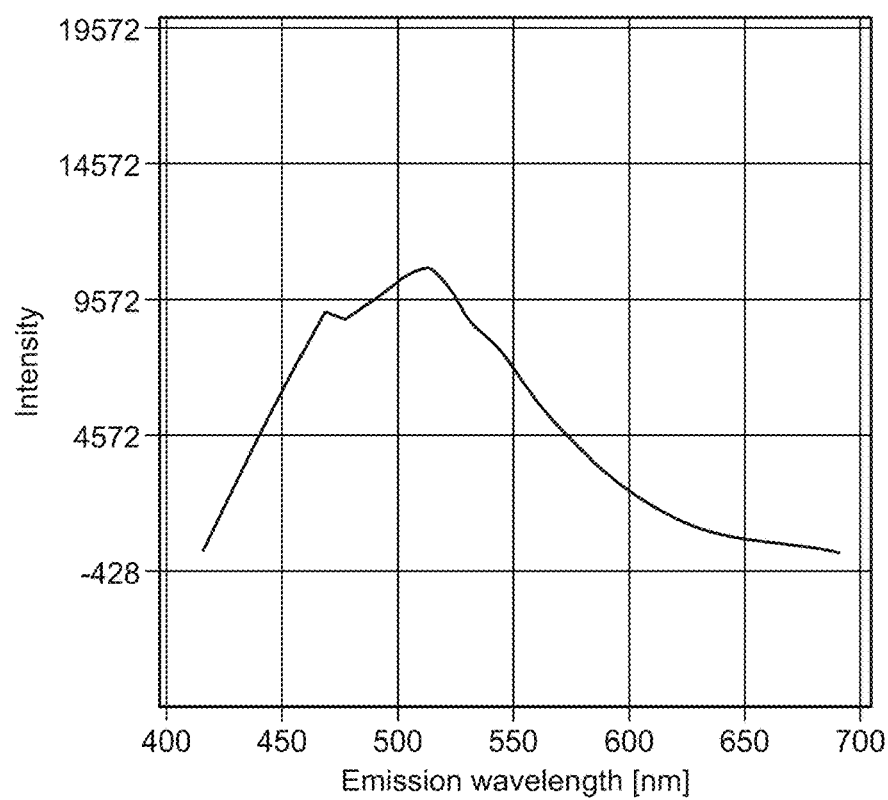
FIG. 7B is a diagram of a fluorescence spectrum of *S. mitis* detected when being irradiated with excitation light having a wavelength of 405 nm.

FIG. 7A is a view of a fluorescence image of *S. mitis* photographed when excitation light having a wavelength of 405 nm is output. FIG. 7B is a diagram of a fluorescence spectrum of *S. mitis* detected when being irradiated with excitation light having a wavelength of 405 nm and illustrates the fluorescence spectrum at a specified position $P_I1$ illustrated in FIG. 7A.

Figure 8A:
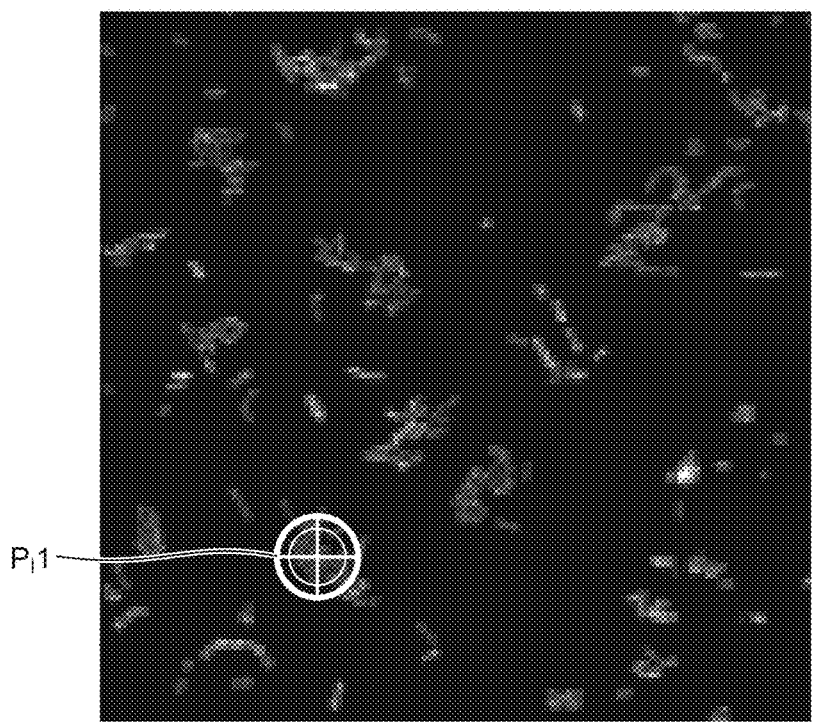
FIG. 8A is a view of a fluorescence image of *S. mitis* photographed when being irradiated with excitation light having a wavelength of 458 nm.
Figure 8B:
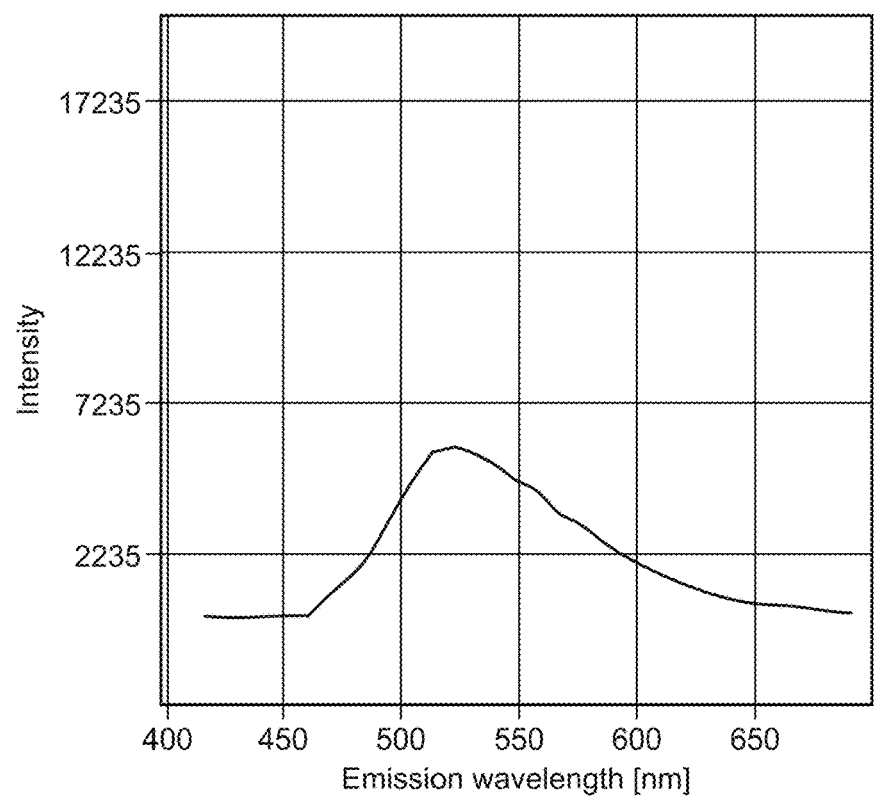
FIG. 8B is a diagram of a fluorescence spectrum of *S. mitis* detected when being irradiated with excitation light having a wavelength of 458 nm.
Figure 9A:
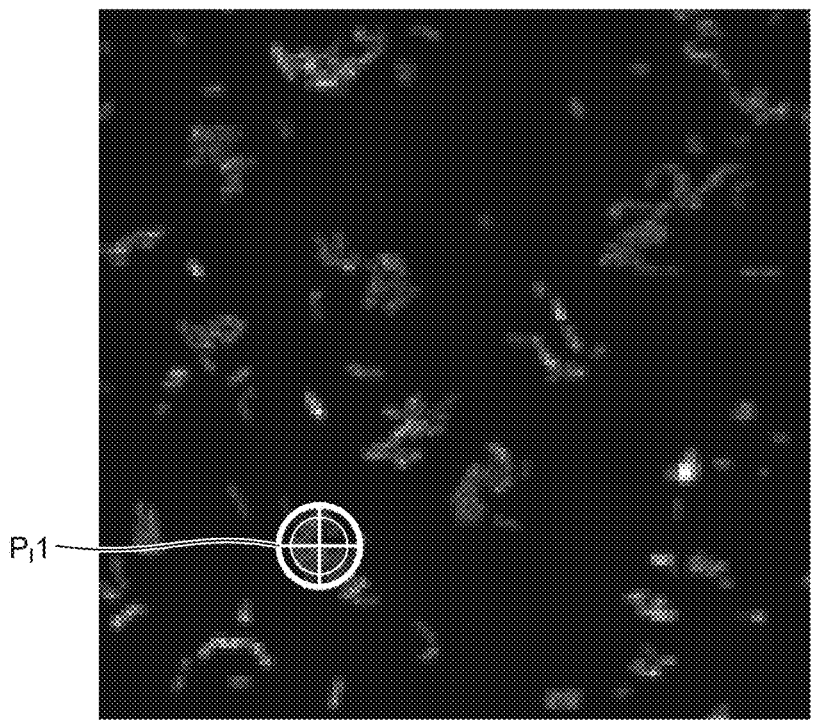
FIG. 9A is a view of a fluorescence image of *S. mitis* photographed when being irradiated with excitation light having a wavelength of 488 nm.
Figure 9B:
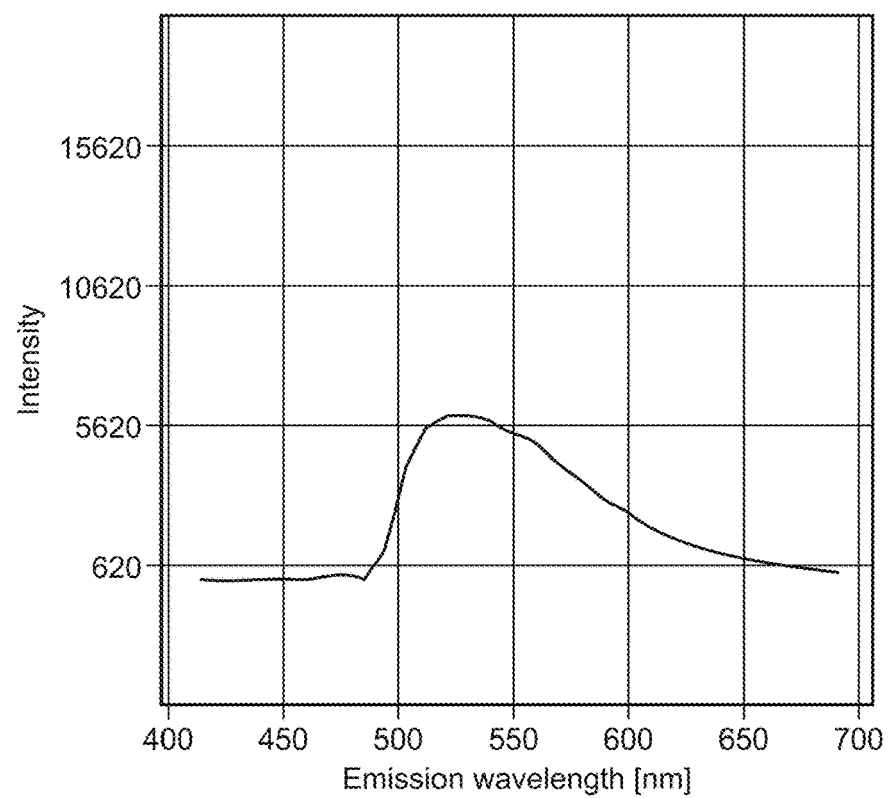
FIG. 9B is a diagram of a fluorescence spectrum of *S. mitis* detected when being irradiated with excitation light having a wavelength of 488 nm.

Similarly, FIGS. 8A and 8B and FIGS. 9A and 9B illustrate fluorescence images and fluorescence spectra obtained when laser light having wavelengths of 458 nm and 488 mm, respectively, are output. FIG. 8A is a view of a fluorescence image of *S. mitis* photographed when excitation light having a wavelength of 458 nm is output. FIG. 8B is a diagram of a fluorescence spectrum of *S. mitis* detected when being irradiated with excitation light having a wavelength of 458 nm and illustrates the fluorescence spectrum at the specified position $P_I1$ illustrated in FIG. 8A. FIG. 9A is a view of a fluorescence image of *S. mitis* photographed when excitation light having a wavelength of 488 nm is output. FIG. 9B is a diagram of a fluorescence spectrum of *S. mitis* detected when being irradiated with excitation light having a wavelength of 488 nm and illustrates the fluorescence spectrum at the specified position $P_I1$ illustrated in FIG. 9A.

As illustrated in FIGS. 7B, 8B, and 9B, different fluorescence spectra are obtained depending on the excitation wavelength. *S. mitis* has unique patterns of autofluorescence generated by the excitation light having wavelengths of 405 nm, 458 nm, and 488 nm as illustrated in the figures.

Figure 10:
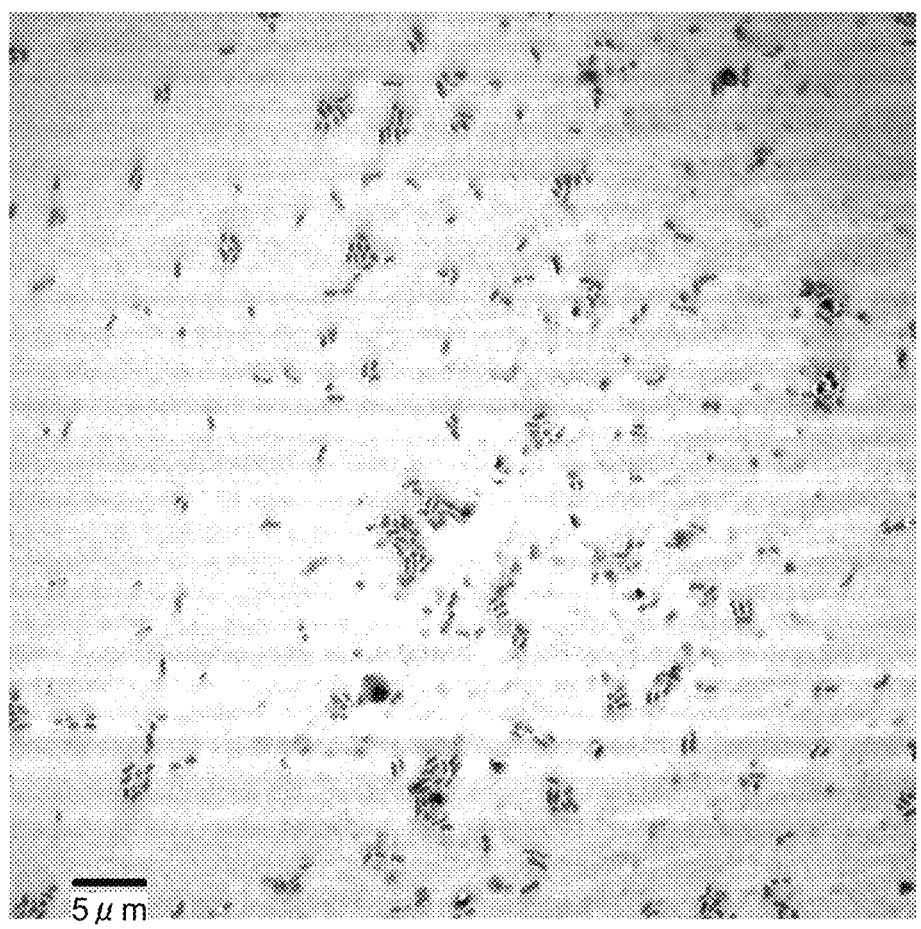
FIG. 10 is a view of a specimen image including Aggregatibacter actinomycetemcomitans (A.a.) serving as an example of the object to be identified by the microscopic system according to the embodiment of the present invention.

The following describes images and fluorescence spectra of Aggregatibacter actinomycetemcomitans (A.a.) with reference to FIGS. 10 to 13B. FIG. 10 is a view of a specimen image including A.a. serving as an example of the object to be identified by the microscopic system according to the embodiment of the present invention. Similarly to FIG. 6, FIG. 10 illustrates a focused image obtained by outputting laser light having a wavelength or a wavelength band set in advance.

Figure 11A:
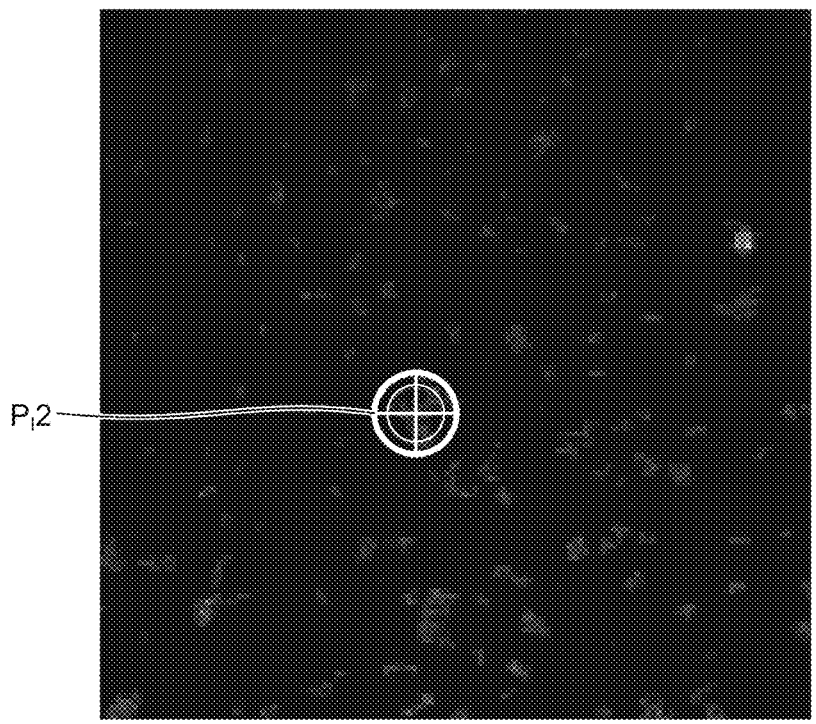
FIG. 11A is a view of a fluorescence image of A.a. photographed when being irradiated with excitation light having a wavelength of 405 nm.
Figure 11B:
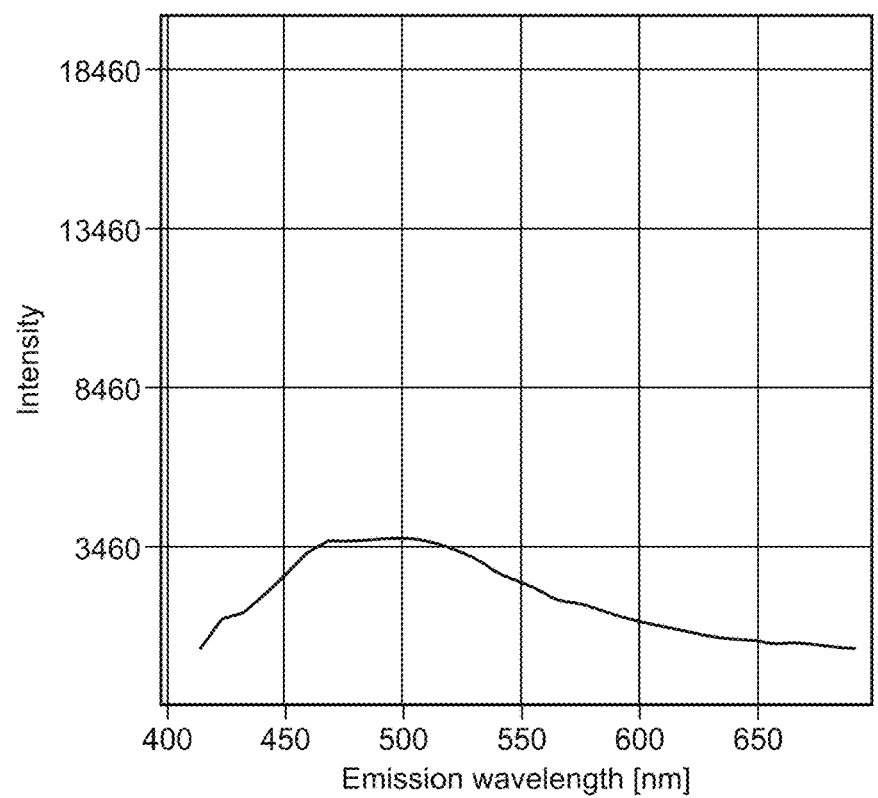
FIG. 11B is a diagram of a fluorescence spectrum of A.a. detected when being irradiated with excitation light having a wavelength of 405 nm.
Figure 12A:
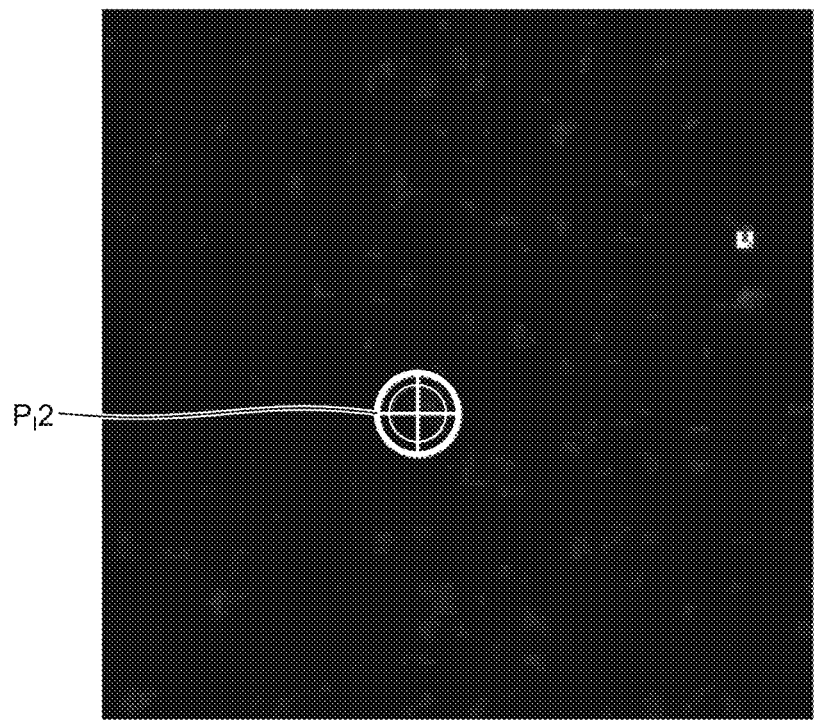
FIG. 12A is a view of a fluorescence image of A.a. photographed when being irradiated with excitation light having a wavelength of 458 nm.
Figure 12B:
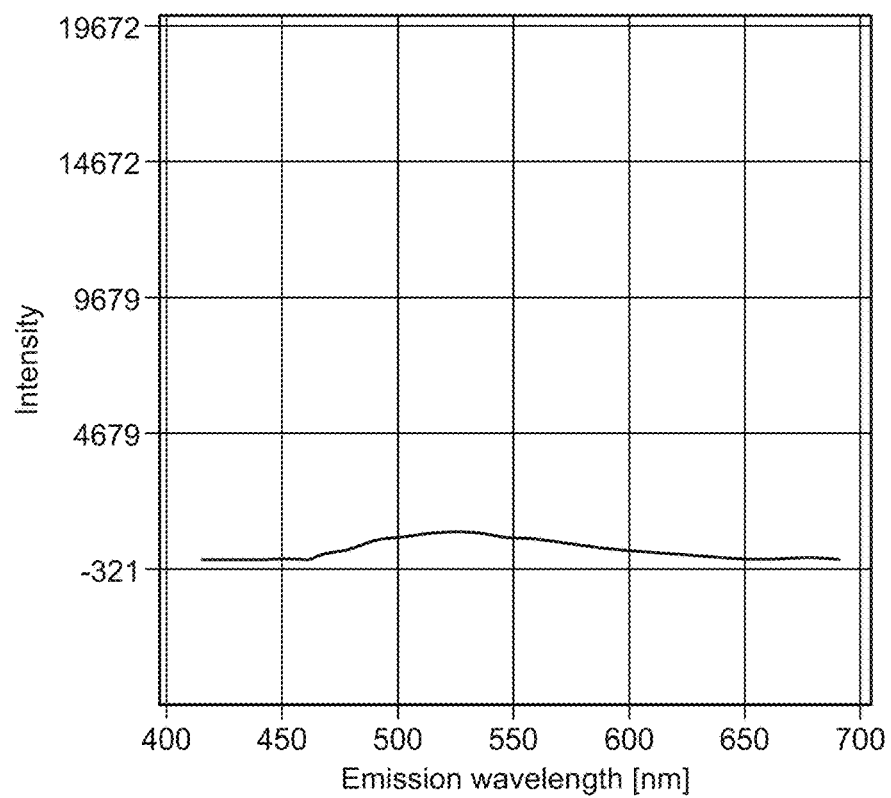
FIG. 12B is a diagram of a fluorescence spectrum of A.a. detected when being irradiated with excitation light having a wavelength of 458 nm.
Figure 13A:
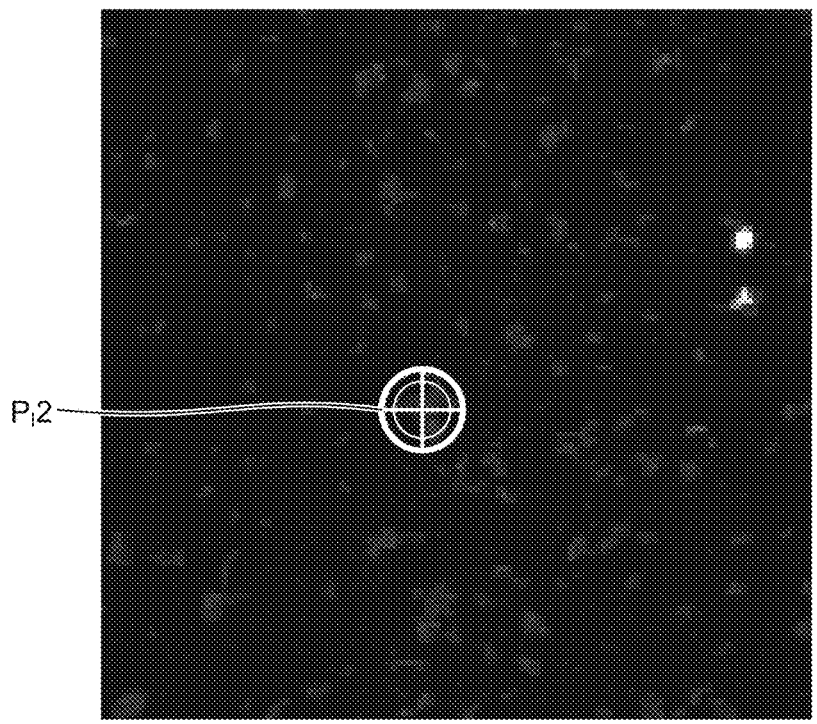
FIG. 13A is a view of a fluorescence image of A.a. photographed when being irradiated with excitation light having a wavelength of 488 nm.
Figure 13B:
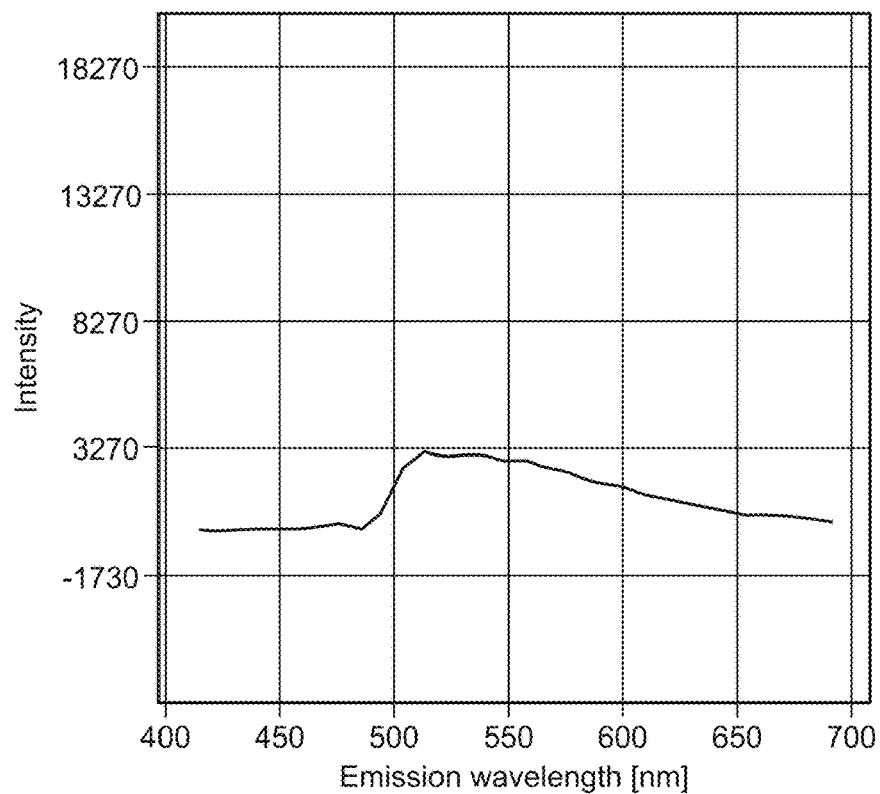
FIG. 13B is a diagram of a fluorescence spectrum of A.a. detected when being irradiated with excitation light having a wavelength of 488 nm.

FIG. 11A is a view of a fluorescence image of A.a. photographed when excitation light having a wavelength of 405 nm is output. FIG. 11B is a diagram of a fluorescence spectrum of A.a. detected when being irradiated with excitation light having a wavelength of 405 nm and illustrates the fluorescence spectrum at a specified position $P_I2$ illustrated in FIG. 11A. FIG. 12A is a view of a fluorescence image of A.a. photographed when excitation light having a wavelength of 458 nm is output. FIG. 12B is a diagram of a fluorescence spectrum of A.a. detected when being irradiated with excitation light having a wavelength of 458 nm and illustrates the fluorescence spectrum at the specified position $P_I2$ illustrated in FIG. 12A. FIG. 13A is a view of a fluorescence image of A.a. photographed when excitation light having a wavelength of 488 nm is output. FIG. 13B is a diagram of a fluorescence spectrum of A.a. detected when being irradiated with excitation light having a wavelength of 488 nm and illustrates the fluorescence spectrum at the specified position $P_I2$ illustrated in FIG. 13A.

As illustrated in FIGS. 11B, 12B, and 13B, different fluorescence spectra are obtained depending on the excitation wavelength. A.a has unique patterns of autofluorescence generated by the excitation light having wavelengths of 405 nm, 458 nm, and 488 nm as illustrated in the figures.

By comparing the fluorescence spectra of *S. mitis* with those of A.a, it is found out that they have different spectrum patterns. As described above, microorganisms each have a unique autofluorescence pattern depending on their kinds.

The data analyzer 305 according to the present embodiment identifies the species of a microorganism based on the obtained autofluorescence pattern. The analysis information recorder 308 records therein the identification table associating the patterns of the fluorescence spectra with the respective species of microorganisms. The data analyzer 305 refers to the identification table recorded in the analysis information recorder 308 to identify the species of a microorganism having an input unknown autofluorescence pattern based on its peak position, for example. The data analyzer 305 identifies the species of a microorganism for each of positions in the Z-axis direction or each of the laser light irradiation positions, for example. The data analyzer 305 generates the identification information including the identified kind and the laser light irradiation position. Explanation has been made on the assumption that the spot diameter (irradiation position) of laser light and the pixel position have a one-to-one correspondence. The present embodiment, however, does not necessarily have the aspect described above if it collectively identifies microorganisms at a plurality of pixel positions and on a plurality of focused images disposed side by side in the Z-axis direction by thinning scanning, for example.

Figure 14:
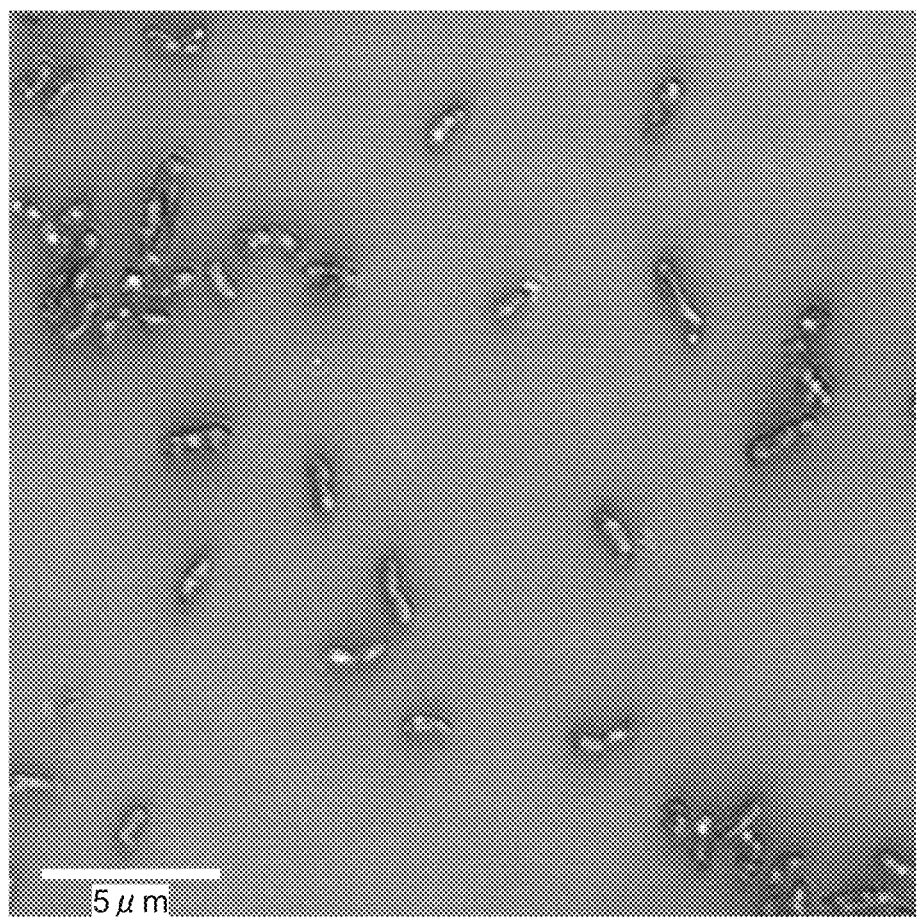
FIG. 14 is a view of a focused image in which *S. mitis* and A.a. are present.
Figure 15:
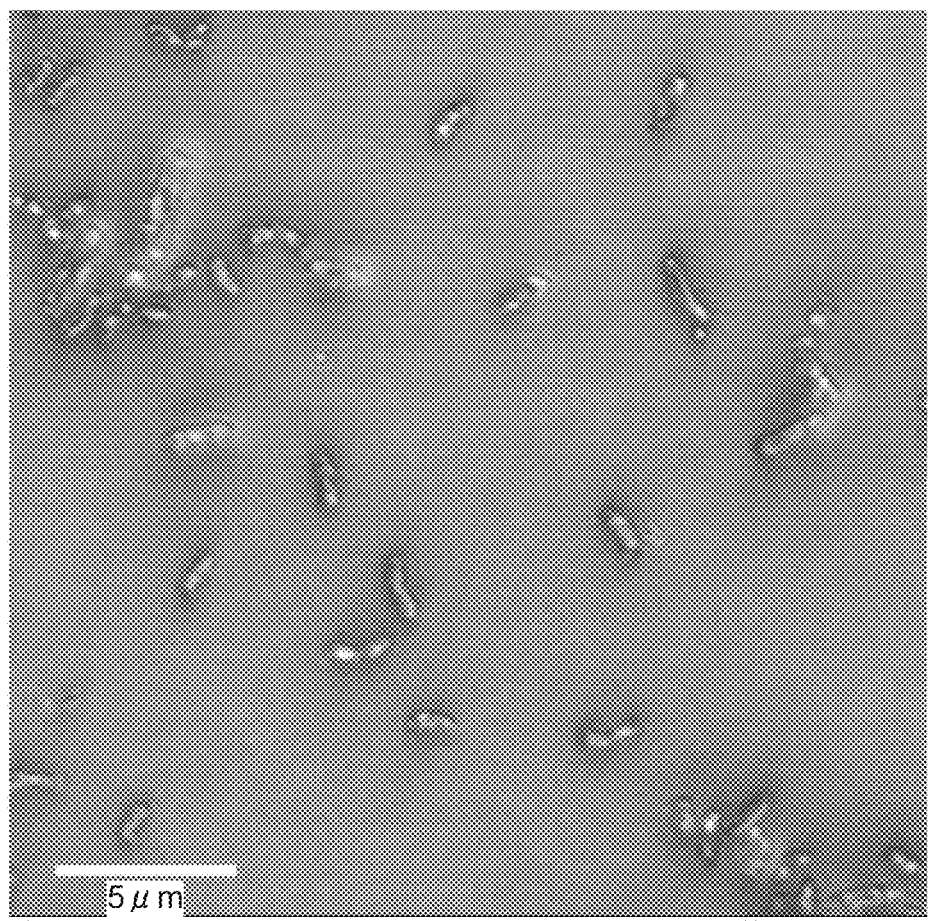
FIG. 15 is a view of an image obtained by coloring *S. mitis* in the focused image illustrated in FIG. 14.

The following describes the superimposition of hues described above, that is, a case where hues are superimposed on a focused image serving as a two-dimensional image with reference to FIGS. 14 and 15. FIG. 14 is a view of a focused image in which *S. mitis* and A.a. are present. As illustrated in FIG. 14, the presence positions of the microorganisms can be grasped on the focused image, but *S. mitis* and A.a fails to be distinguished from each other only by receiving autofluorescence and imaging it.

FIG. 15 is a view of an image obtained by coloring *S. mitis* in the focused image illustrated in FIG. 14. If the hue superimposer 306 superimposes red on the positions identified as *S. mitis* in the focused image illustrated in FIG. 14, *S. mitis* can be identified from the mixed microorganisms. In addition, if it is found out that only *S. mitis* and A.a. are present in the image, the other microorganisms can be identified as A.a.

Figure 16:
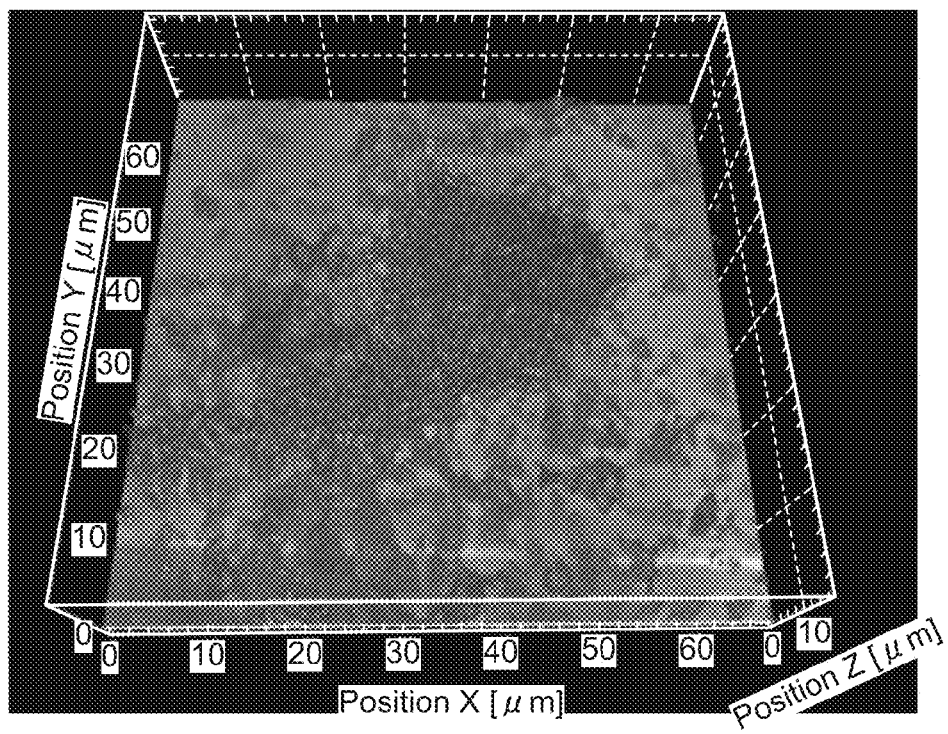
FIG. 16 is a view of a three-dimensional image three-dimensionally representing a plurality of focused images in which *S. mitis* and A.a. are present.
Figure 17:
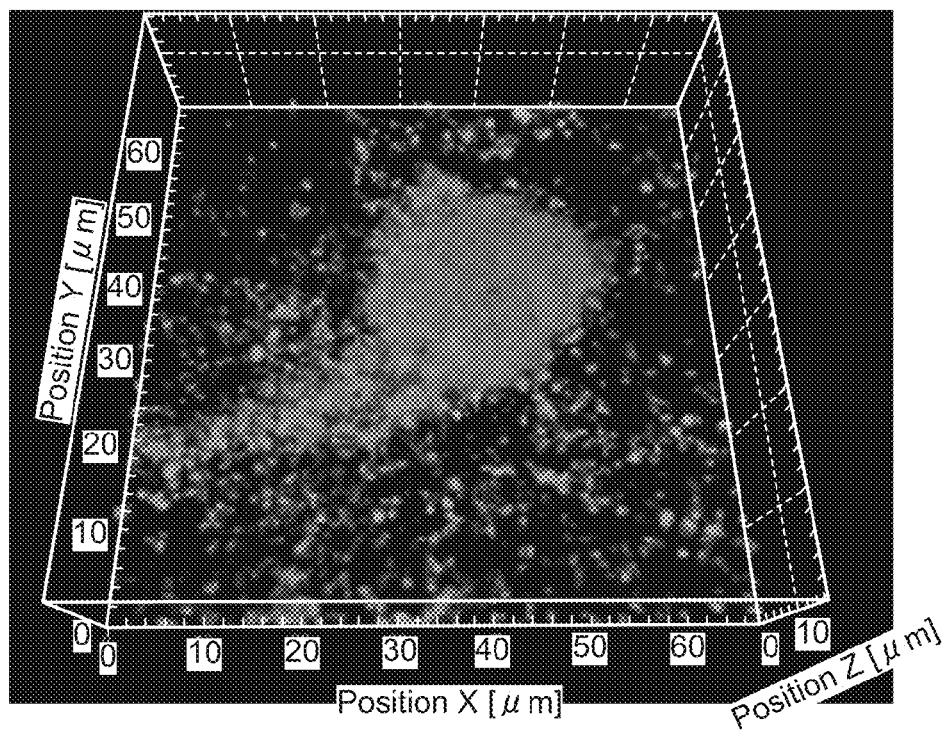
Figure 18:
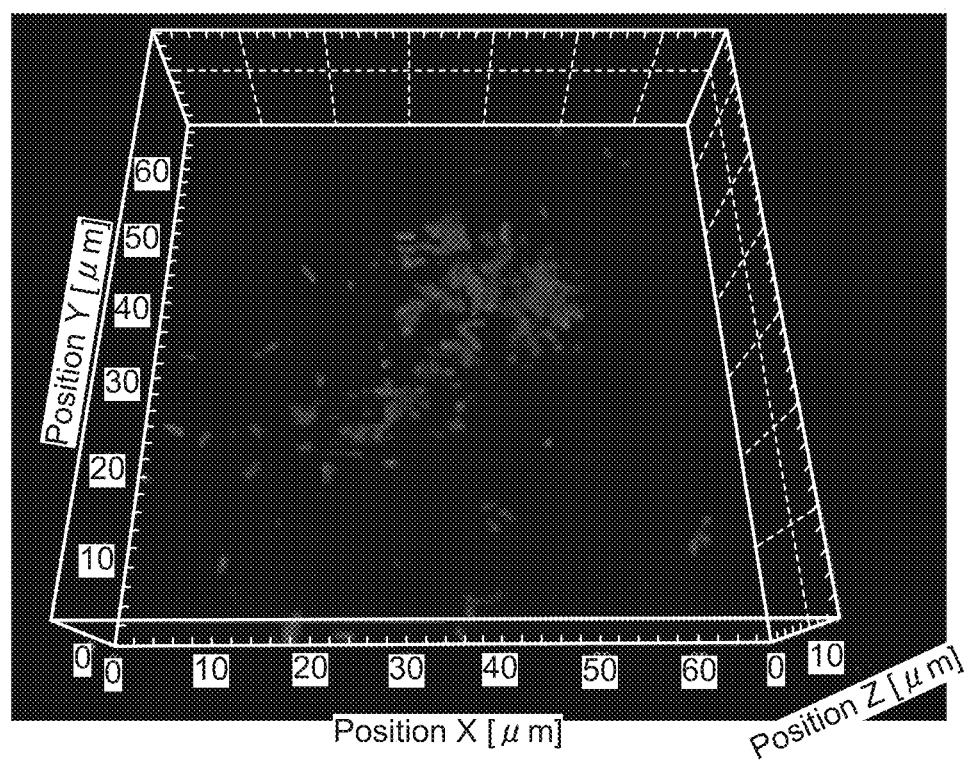
FIG. 18 is a view of a three-dimensional image obtained by extracting *S. mitis* from the three-dimensional image illustrated in FIG. 17.
Figure 19:
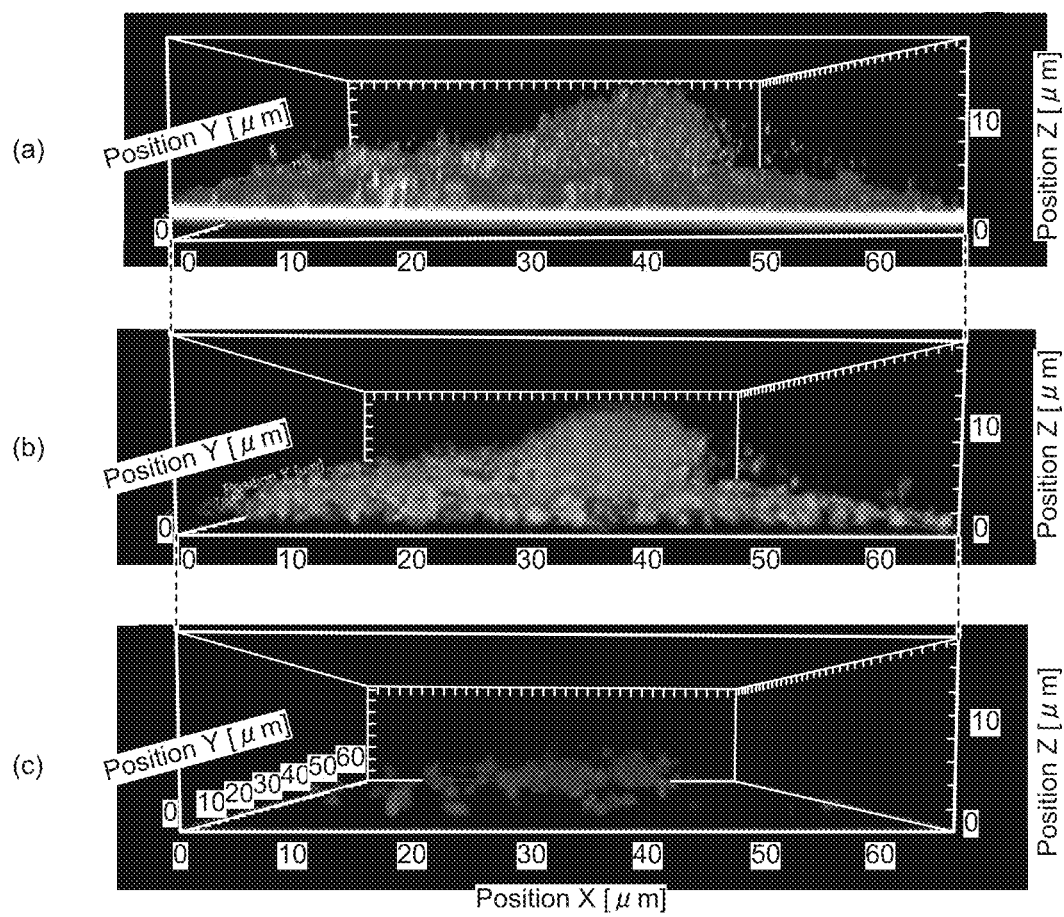
FIG. 19(*a*) is a three-dimensional image based on reflected light, FIG. 19(*b*) is a three-dimensional image obtained by coloring *S. mitis* and A.a, and FIG. 19(*c*) is a three-dimensional image obtained by coloring *S. mitis*.

The following describes a case where the color superimposition described above is performed on a three-dimensional image with reference to FIGS. 16 to 19. FIG. 16 is a view of a three-dimensional image three-dimensionally representing a plurality of focused images in which *S. mitis* and A.a. are present. FIG. 17 is a view of a three-dimensional image obtained by coloring *S. mitis* and A.a. FIG. 18 is a view of a three-dimensional image obtained by extracting *S. mitis* from the three-dimensional image illustrated in FIG. 17. FIG. 19 is a three-dimensional image based on reflected light, and FIG. 19(a) is a three-dimensional image not subjected to coloring corresponding to the species of microorganisms, FIG. 19(b) is a three-dimensional image obtained by coloring *S. mitis* and A.a, and FIG. 19(c) is a three-dimensional image obtained by coloring *S. mitis*.

In the three-dimensional images illustrated in FIGS. 16 and 19(a), similarly to the focused image illustrated in FIG. 14, the spatial positions of the microorganisms can be grasped on the three-dimensional image, but *S. mitis* and A.a fails to be distinguished from each other.

If the hue superimposer 306 superimposes red on *S. mitis* and green on A.a. in the three-dimensional images illustrated in FIGS. 16 and 19(a), *S. mitis* and A.a can be identified in the space where the microorganisms are mixed (refer to FIGS. 17 and 19(b)). By extracting *S. mitis* as illustrated in FIGS. 18 and 19(c), the positions of *S. mitis* present behind A.a. in a line-of-sight direction (e.g., the Y-axis direction in FIG. 19(c)) can be spatially grasped.

The image generation described above can be performed by the confocal laser scanning microscope 100 outputting laser light and receiving reflected light or autofluorescence emitted by the specimen. As a result, the present embodiment can identify microorganisms without isolating or culturing microorganisms or determining their base sequences like in the conventional techniques. In particular, the present embodiment enables observing live microorganisms without any change and identifying them. Consequently, the present embodiment can follow the dynamic state (e.g., growth and movement) of microorganisms chronologically. By chronologically generating the three-dimensional image data illustrated in FIG. 15, for example, and switching the images in time-series to display video, the present embodiment enables observing chronological movement of the microorganisms. By coloring identified microorganisms, the present embodiment can follow the dynamic state of a specific microorganism in a mixture of a plurality of microorganisms.

Besides identifying the kinds as described above, the data analyzer 305 can evaluate the state of the specimen and perform an analysis, such as clustering. The following describes examples of the analysis processing performed by the data analyzer 305 with reference to the drawings.

Figure 20:
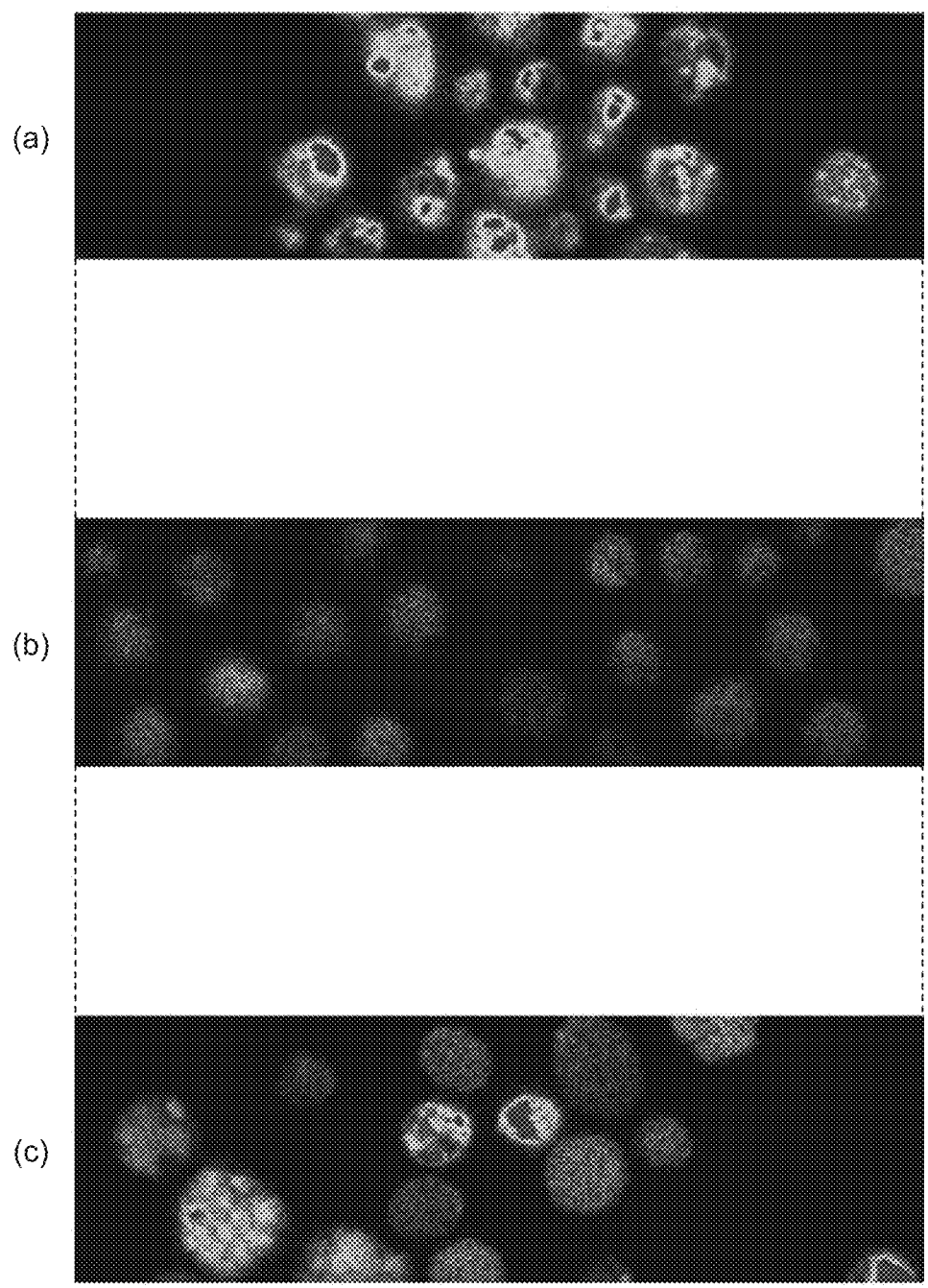
FIG. 20 is an image displaying oleaginous yeast (Ascomycete) having different properties, and FIG. 20(*a*) is a view of an autofluorescence image of a high lipid-producing strain, FIG. 20(*b*) is a view of an autofluorescence image of a low lipid-accumulating strain, and FIG. 20(*c*) is a view of an autofluorescence image obtained by mixing the high lipid-producing strain and the low lipid-accumulating strain.

FIG. 20 is an image displaying Lipomyces starkey serving as oleaginous yeast (Ascomycete) having different properties, and FIG. 20(a) is a view of an autofluorescence image of a high lipid-producing strain, FIG. 20(b) is a view of an autofluorescence image of a low lipid-accumulating strain, and FIG. 20(c) is a view of an autofluorescence image obtained by mixing the high lipid-producing strain and the low lipid-accumulating strain. As illustrated in FIG. 20, Ascomycete of a high lipid-producing strain that highly produces lipid (refer to FIG. 20(a)) and Ascomycete of a low lipid-accumulating strain that has relatively low lipid accumulation ability (refer to FIG. 20(b)) are different in color (wavelength) of autofluorescence and in size of fungi (refer to FIG. 20(c)).

Figure 21:
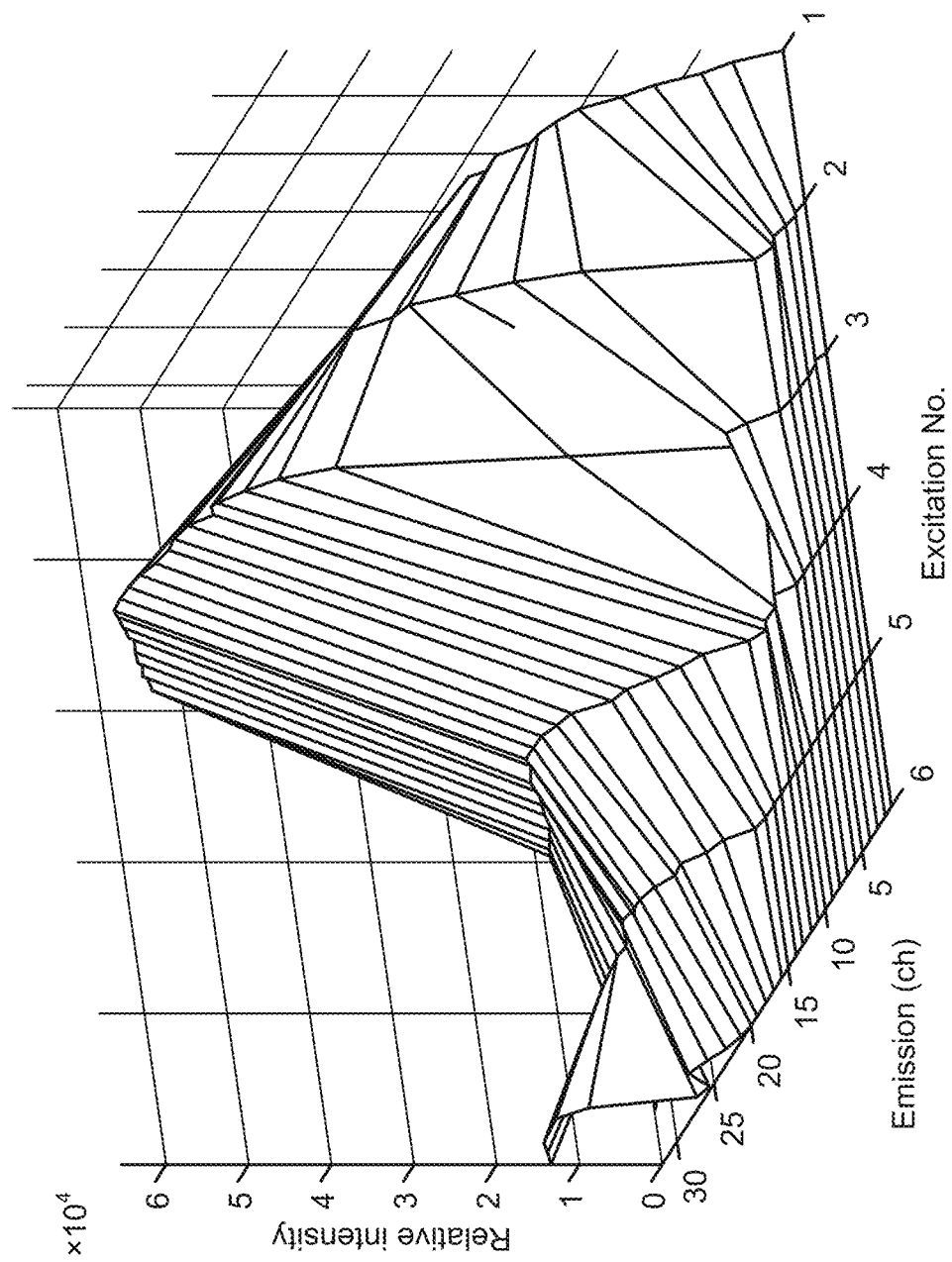
FIG. 21 is a diagram indicating a spectrum profile of autofluorescence of the high lipid-producing strain illustrated in FIG. 20(*a*).
Figure 22:
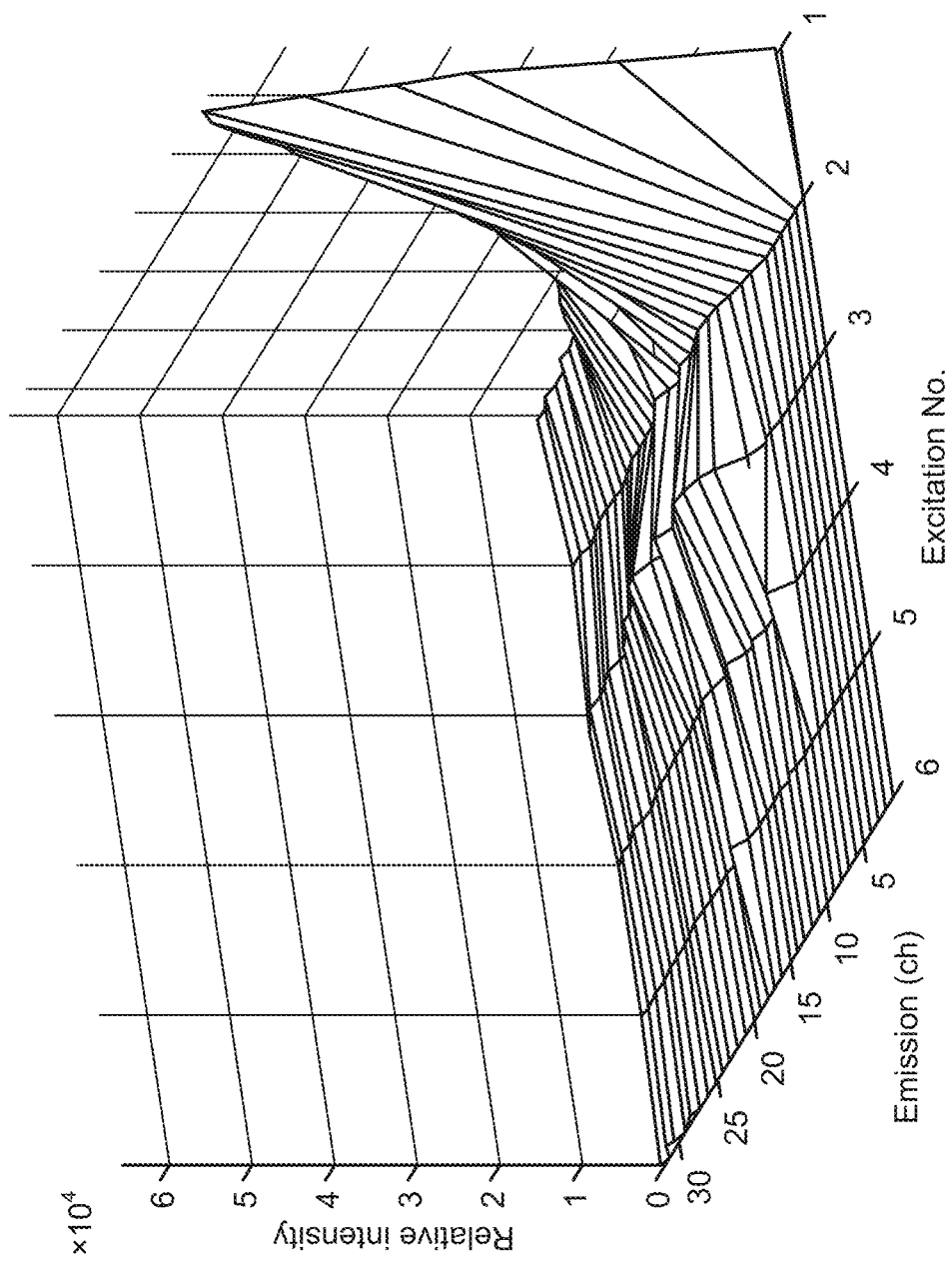
FIG. 22 is a diagram indicating a spectrum profile of autofluorescence of the low lipid-accumulating strain illustrated in FIG. 20(*b*).

FIG. 21 is a diagram indicating a spectrum profile of autofluorescence of the high lipid-producing strain illustrated in FIG. 20(a). FIG. 22 is a diagram indicating a spectrum profile of autofluorescence of the low lipid-accumulating strain illustrated in FIG. 20(b). FIGS. 21 and 22 illustrate a three-dimensional Cartesian coordinate system in which a first axis, a second axis, and a third axis are orthogonal to one another. The first axis indicates number (Excitation No.) assigned to the wavelength (wavelength band) of used excitation light. The second axis indicates number (Emission (ch)) of wavelength band of autofluorescence divided corresponding to the optical resolution (32 channels in the embodiment) of the detector 109. The third axis indicates relative intensity of autofluorescence of the detected channels. As illustrated in FIGS. 21 and 22, the fluorescence spectra of the respective strains are represented by the three-dimensional distributions of the relative intensity of autofluorescence and are different between the high lipid-producing strain and the low lipid-accumulating strain.

Figure 23:
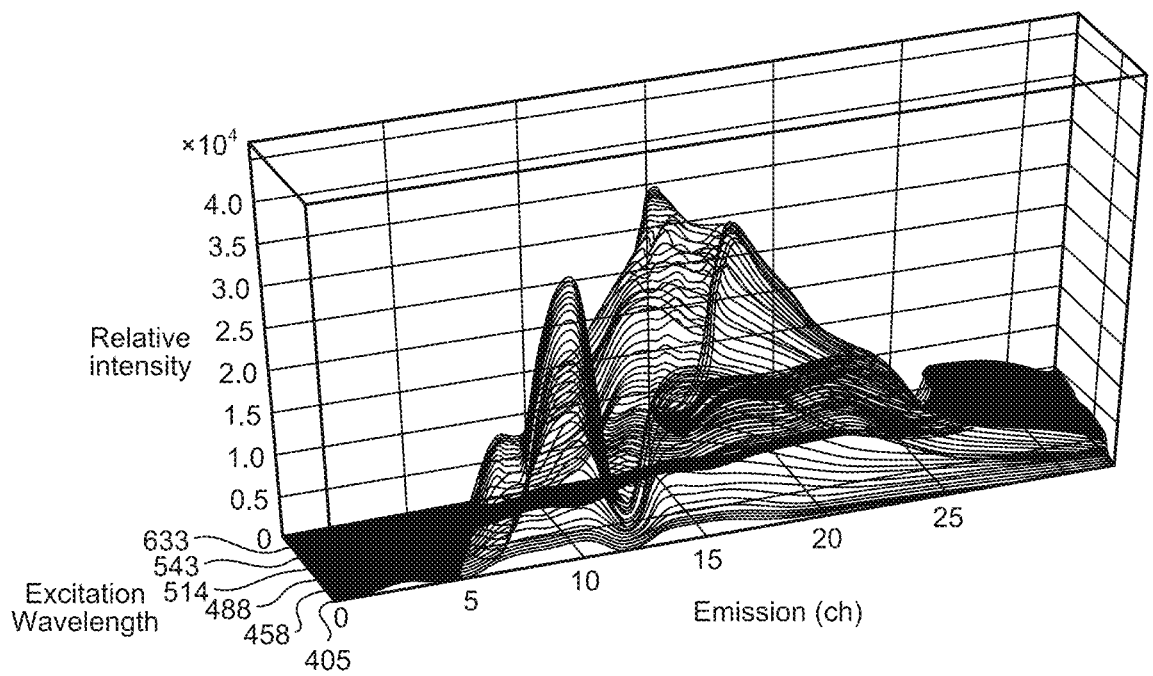
FIG. 23 is a diagram indicating a spectrum profile of autofluorescence of *Paenibacillus polymyxa* serving as a soil bacterium.
Figure 24:
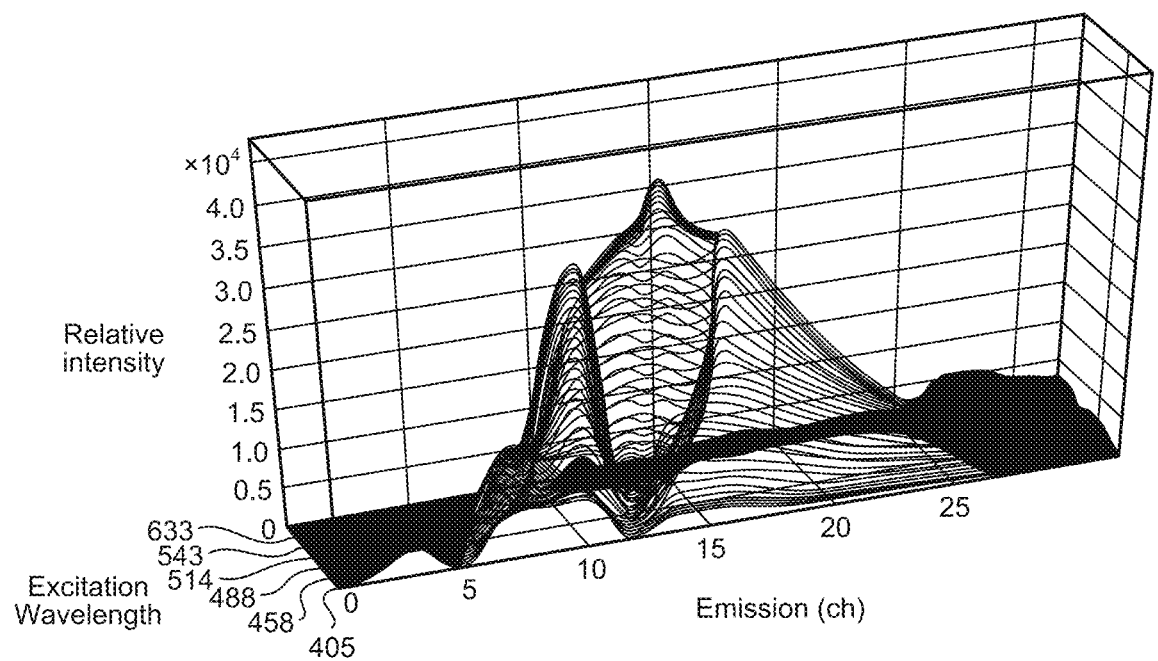
FIG. 24 is a diagram indicating a spectrum profile of autofluorescence of *Pseudomonas putida* serving as a soil bacterium.

FIG. 23 is a diagram indicating a spectrum profile of autofluorescence of *Paenibacillus polymyxa* serving as a soil bacterium. FIG. 24 is a diagram indicating a spectrum profile of autofluorescence of *Pseudomonas putida* serving as a soil bacterium. Similarly to FIGS. 21 and 22, FIGS. 23 and 24 also illustrate the three-dimensional Cartesian coordinate system in which the first axis, the second axis, and the third axis are orthogonal to one another. The first axis indicates number (Excitation No.) assigned to the wavelength (wavelength band) of used excitation light. The second axis indicates wavelength band (Emission Wavelength) of autofluorescence divided corresponding to the optical resolution (32 channels) of the detector 109. The third axis indicates relative intensity of autofluorescence of the detected channels. *Paenibacillus polymyxa* is a Gram-positive bacterium. *Pseudomonas putida* is a Gram-negative bacterium. As illustrated in FIGS. 23 and 24, the soil bacteria also have different distributions of the relative intensity of autofluorescence depending on their kinds.

The analysis information recorder 308 records therein such distributions of the relative intensity in a manner associated with the states of the strain, for example. The data analyzer 305 compares the pattern of autofluorescence obtained by the detection signals with the distributions of the relative intensity recorded in the analysis information recorder 308. The data analyzer 305 thus evaluates the state of the strain, which is the lipid accumulation ability in this example, and identifies the soil bacterium.

Figure 25A:
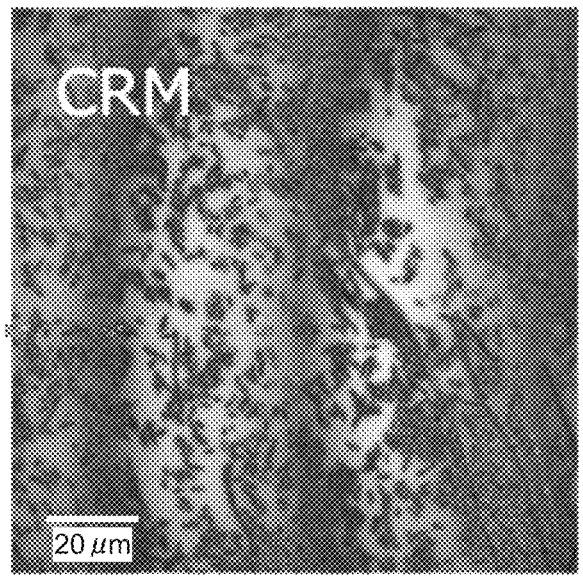
FIG. 25A is a view of a confocal reflection microscopy image of wild-type strain of *Escherichia coli*.
Figure 25B:
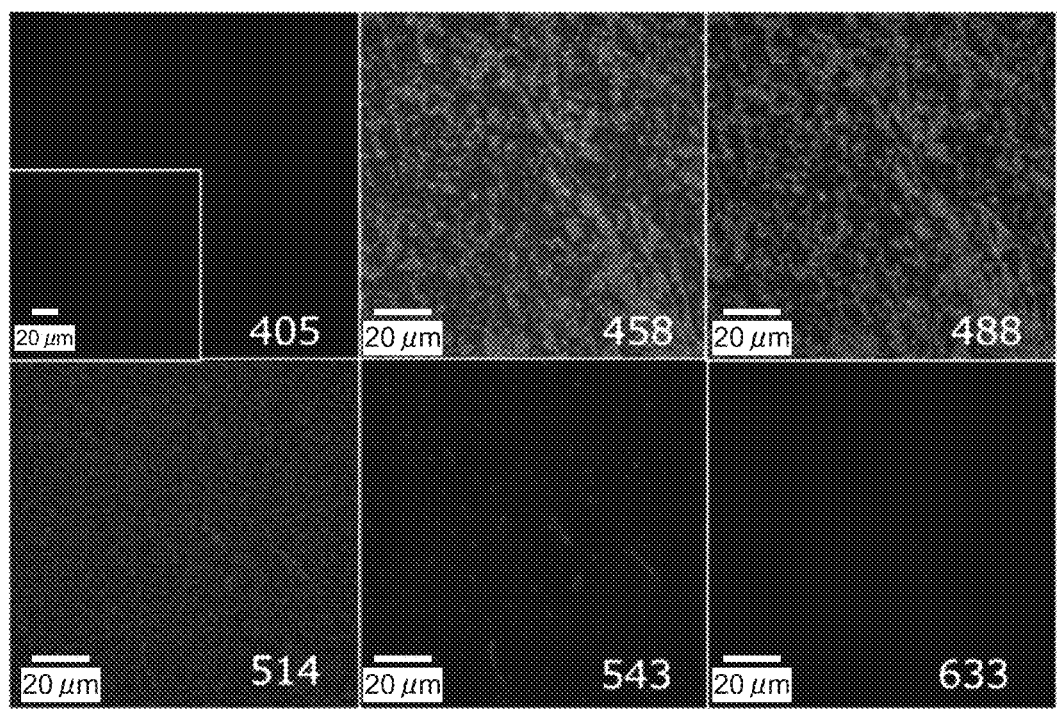
FIG. 25B is a view of autofluorescence images of the wild-strain *Escherichia coli* obtained when being irradiated with respective rays of excitation light.

A wild strain of *Escherichia coli* (hereinafter, referred to as wild-strain *Escherichia coli*) and a tyrosine overproducing strain of *Escherichia coli* (hereinafter, referred to as tyrosine-overproducing-strain *Escherichia coli*) are also different in color of autofluorescence (intensity distribution with respect to the wavelength). FIG. 25A is a view of a confocal reflection microscopy image of wild-strain *Escherichia coli*. FIG. 25B is a view of autofluorescence images of the wild-strain *Escherichia coli* obtained when being irradiated with respective rays of excitation light. The images illustrated in FIGS. 25A and 25B are images obtained when the same scanning plane is scanned. FIG. 25B illustrates the autofluorescence images obtained when the excitation light is output with wavelengths of 405 nm, 458 nm, 488 nm, 514 nm, 543 nm, and 633 nm.

Figure 26A:
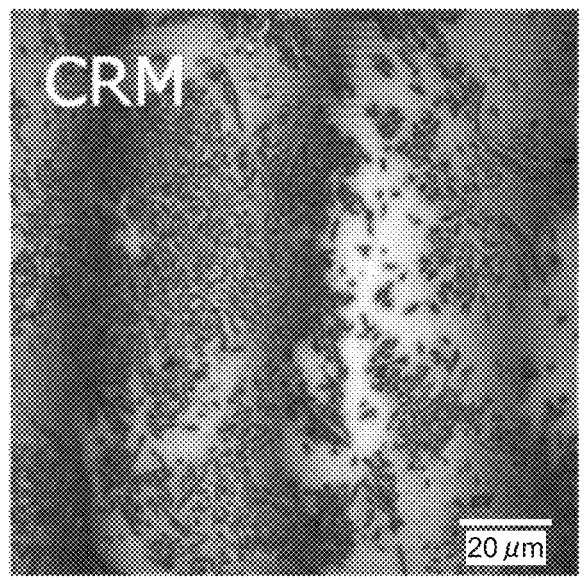
FIG. 26A is a view of a confocal reflection microscopy image of tyrosine-overproducing-strain of *Escherichia coli*.
Figure 26B:
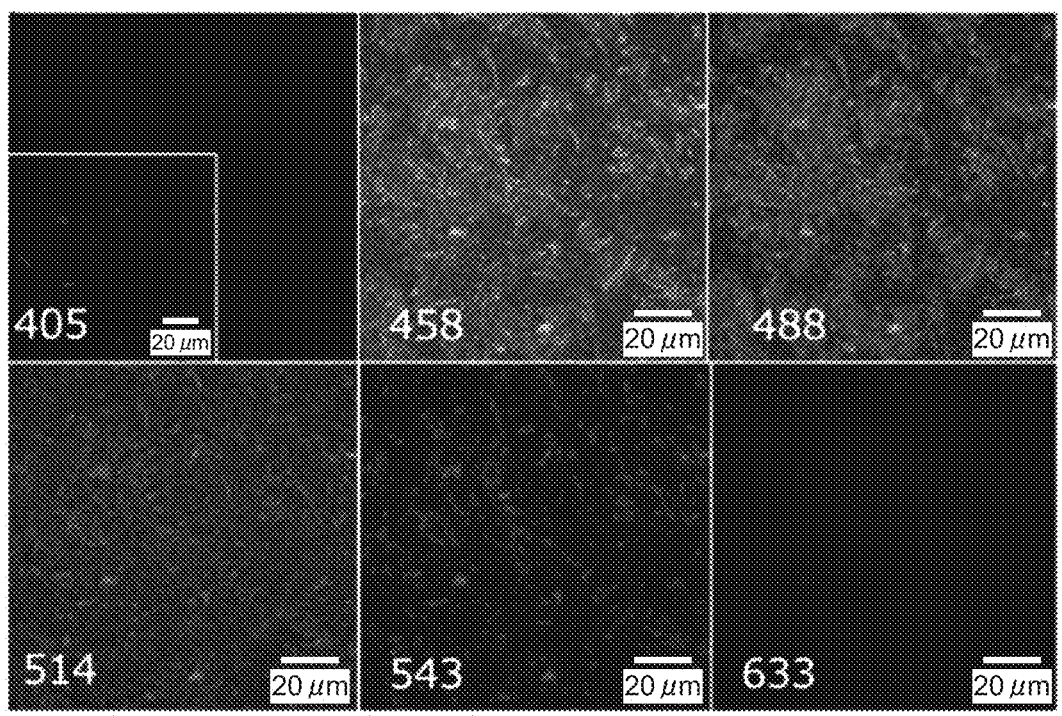
FIG. 26B is a view of autofluorescence images of the tyrosine-overproducing-strain *Escherichia coli* obtained when being irradiated with respective rays of excitation light.

FIG. 26A is a view of a confocal reflection microscopy image of tyrosine-overproducing-strain *Escherichia coli*. FIG. 26B is a view of autofluorescence images of the tyrosine-overproducing-strain *Escherichia coli* obtained when being irradiated with respective rays of excitation light. The images illustrated in FIGS. 26A and 26B are images obtained when the same scanning plane is scanned. FIG. 26B illustrates the autofluorescence images obtained when the excitation light is output with wavelengths of 405 nm, 458 nm, 488 nm, 514 nm, 543 nm, and 633 nm.

As illustrated in FIGS. 25B and 26B, the fluorescence patterns are significantly different in fluorescence intensity or color when the wavelength of the excitation light is 514 nm and 543 nm. Based on the difference, the present embodiment can distinguish the two kinds of *Escherichia coli* in a mixture of wild-strain *Escherichia coli* and tyrosine-overproducing-strain *Escherichia coli*, for example, based on the intensity distributions of autofluorescence obtained from the specimen.

Figure 27:
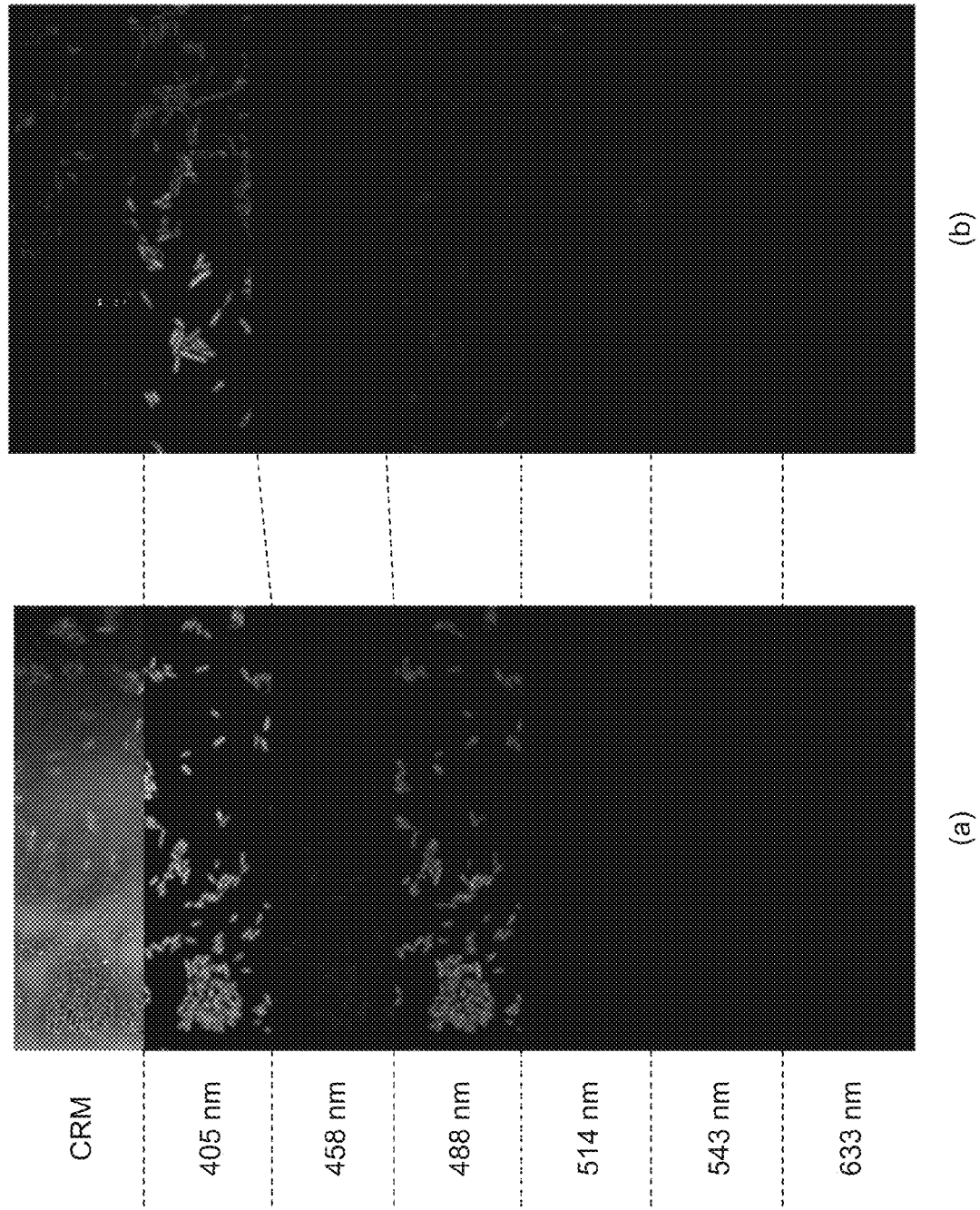
FIG. 27(*a*) is a view of confocal reflection microscopy images and autofluorescence images of the wild-strain *Escherichia coli*, and FIG. 27(*b*) is a view of confocal reflection microscopy images and autofluorescence images of the tyrosine-overproducing-strain of *Escherichia coli*.

A wild-strain *Escherichia coli* and a mutant strain of *Escherichia coli* (hereinafter, referred to as mutant-strain *Escherichia coli*) are also different in pattern of autofluorescence. FIG. 27(a) is a view of confocal reflection microscopy images and autofluorescence images of the wild-strain *Escherichia coli*, and FIG. 27(b) is a view of confocal reflection microscopy images and autofluorescence images of the tyrosine-overproducing-strain *Escherichia coli*. FIG. 27 illustrates the autofluorescence images obtained when the excitation light is output with wavelengths of 405 nm, 458 nm, 488 nm, 514 nm, 543 nm, and 633 nm.

As illustrated in FIGS. 27(a) and 27(b), the autofluorescence patterns are significantly different in fluorescence intensity especially when the wavelength of the excitation light is 488 nm. Based on the difference, the present embodiment can distinguish the two kinds of *Escherichia coli* in a mixture of wild-strain *Escherichia coli* and mutant-strain *Escherichia coli*, for example, based on the autofluorescence patterns obtained from the specimen.

Figure 28A:
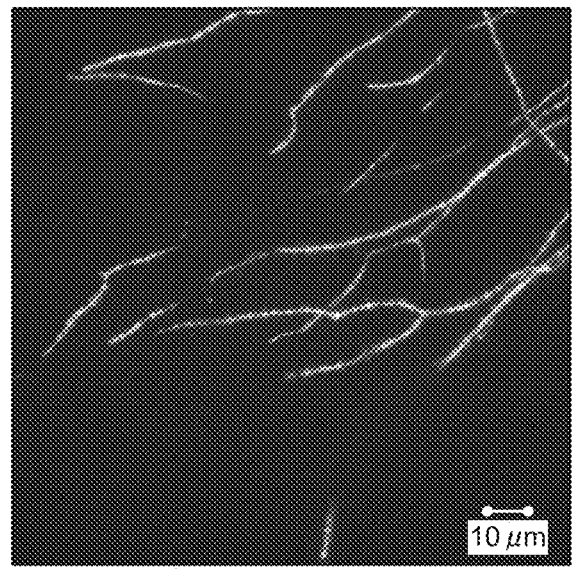
FIG. 28A is a view of a confocal reflection microscopy image of a wild strain of a filamentous fungus(*Aspergillus nidulans*).
Figure 28B:
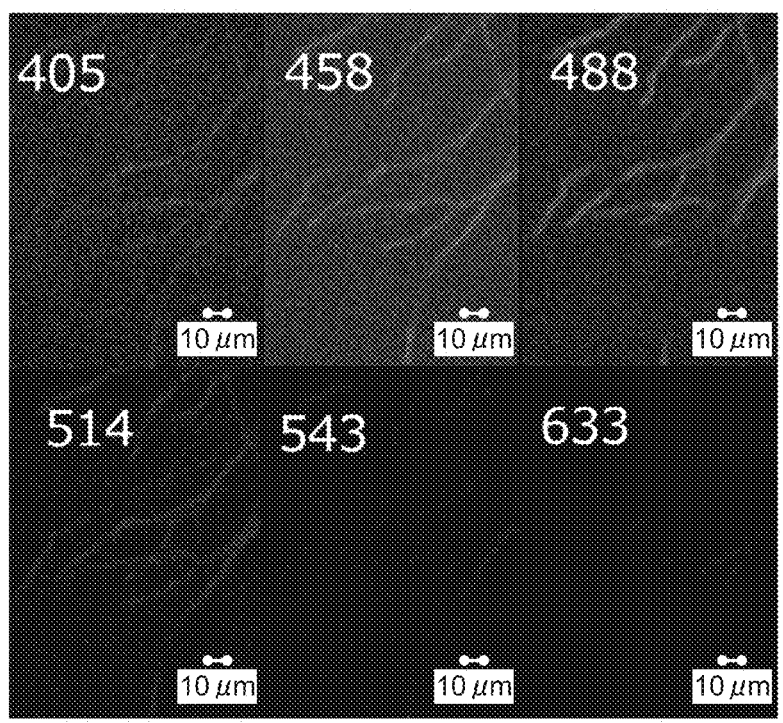
FIG. 28B is a view of autofluorescence images of the wild strain of the filamentous fungus (*Aspergillus nidulans*) obtained when being irradiated with respective rays of excitation light.

A wild strain of a filamentous fungus (*Aspergillus nidulans*) and a mutant strain of a filamentous fungus (*Aspergillus nidulans*) are also different in color of autofluorescence (intensity distribution with respect to the wavelength). FIG. 28A is a view of a confocal reflection microscopy image of a wild strain of a filamentous fungus (*Aspergillus nidulans*). FIG. 28B is a view of autofluorescence images of the wild strain of the filamentous fungus (*Aspergillus nidulans*) obtained when being irradiated with respective rays of excitation light.

The images illustrated in FIGS. 28A and 28B are images obtained when the same scanning plane is scanned. FIG. 28B illustrates the autofluorescence images obtained when the excitation light is output with wavelengths of 405 nm, 458 nm, 488 nm, 514 nm, 543 nm, and 633 nm.

Figure 29A:
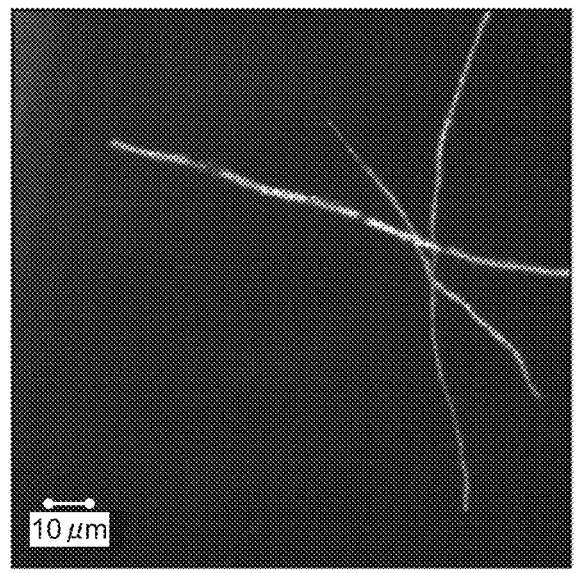
FIG. 29A is a view of a confocal reflection microscopy image of a mutant strain of a filamentous fungus (*Aspergillus nidulans*).
Figure 29B:
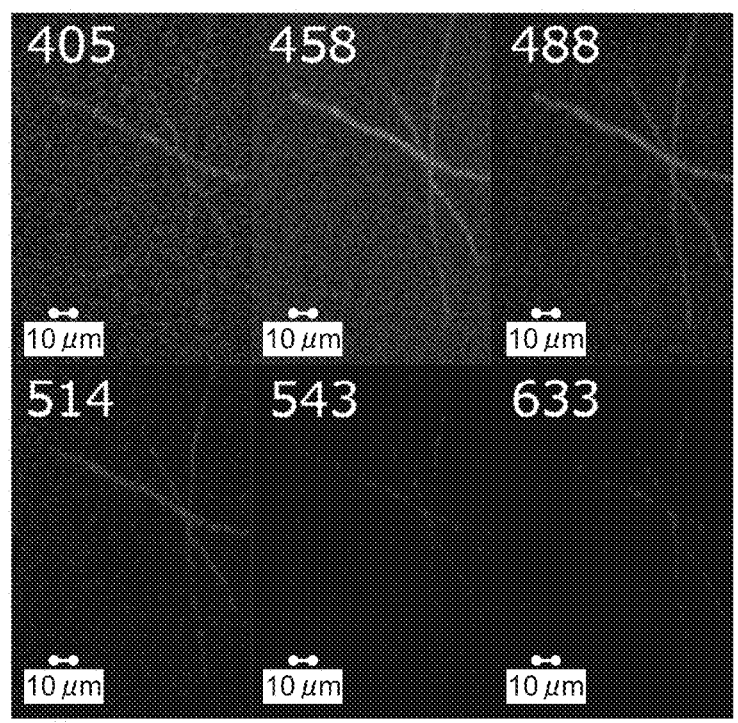
FIG. 29B is a view of autofluorescence images of the mutant strain of the filamentous fungus (*Aspergillus nidulans*) obtained when being irradiated with respective rays of excitation light.

FIG. 29A is a view of a confocal reflection microscopy image of a mutant strain of a filamentous fungus (*Aspergillus nidulans*). FIG. 29B is a view of autofluorescence images of the mutant strain of the filamentous fungus (*Aspergillus nidulans*) obtained when being irradiated with respective rays of excitation light. The images illustrated in FIGS. 29A and 29B are images obtained when the same scanning plane is scanned. FIG. 29B illustrates the autofluorescence images obtained when the excitation light is output with wavelengths of 405 nm, 458 nm, 488 nm, 514 nm, 543 nm, and 633 nm. FIGS. 29A and 29B illustrate a mutant strain with changed nitrogen metabolism ability.

As illustrated in FIGS. 28B and 29B, the wild strain and the mutant strain are significantly different in fluorescence intensity or color especially when the wavelength of the excitation light is 633 nm. Based on the difference, the present embodiment can distinguish the two kinds of *filamentous fungus* in a mixture of wild strain of the *filamentous fungus* and mutant strain of the filamentous fungus, for example, based on the intensity distributions of autofluorescence obtained from the specimen.

Figure 30:
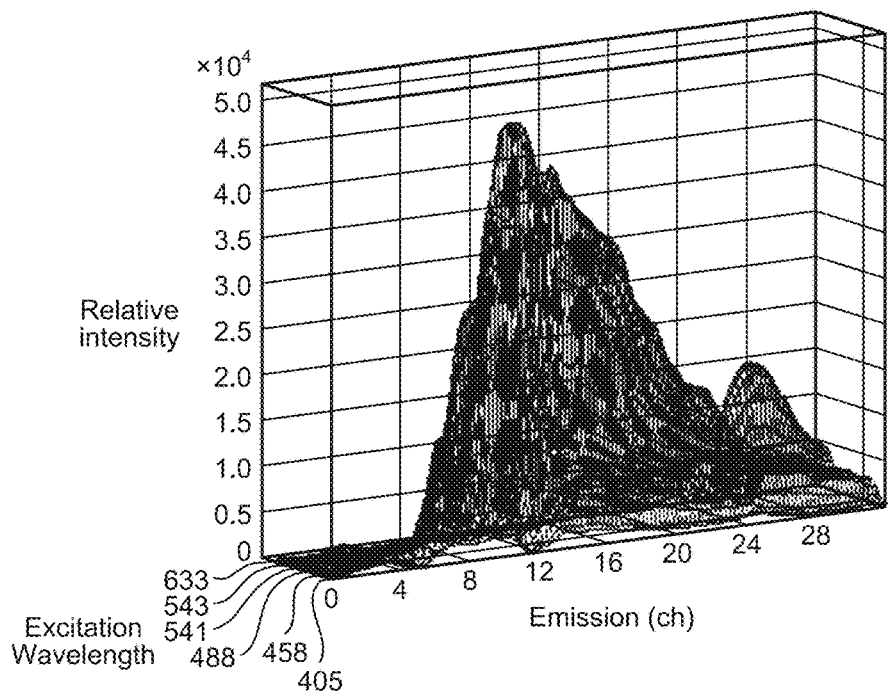
FIG. 30 is a diagram indicating a spectrum profile of autofluorescence of the wild strain of the filamentous fungus (*Aspergillus nidulans*).
Figure 31:
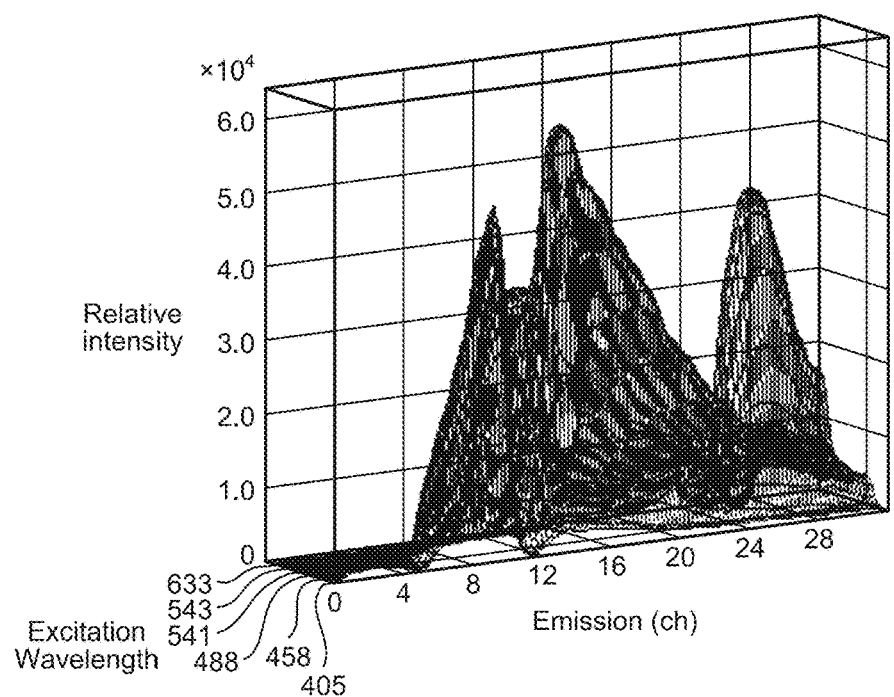
FIG. 31 is a diagram indicating a spectrum profile of autofluorescence of the mutant strain of the filamentous fungus (*Aspergillus nidulans*).

FIG. 30 is a diagram indicating a spectrum profile of autofluorescence of the wild strain of the filamentous fungus (*Aspergillus nidulans*). FIG. 31 is a diagram indicating a spectrum profile of autofluorescence of the mutant strain of the filamentous fungus (*Aspergillus nidulans*). Similarly to FIGS. 23 and 24, FIGS. 30 and 31 also illustrate the three-dimensional Cartesian coordinate system in which the first axis, the second axis, and the third axis are orthogonal to one another. The first axis indicates number (Excitation No.) assigned to the wavelength (wavelength band) of used excitation light. The second axis indicates wavelength band (Emission Wavelength) of autofluorescence divided corresponding to the optical resolution (32 channels) of the detector 109. The third axis indicates relative intensity of autofluorescence of the detected channels. As illustrated in FIGS. 30 and 31, the filamentous fungus (*Aspergillus nidulans*) also have different distributions of the relative intensity of autofluorescence between the wild strain and the mutant strain.

The same wild strain or the same mutant strain has slightly different autofluorescence patterns due to the properties of the light source of output excitation light and individual differences of the strains themselves. As a result, the same wild strain may not possibly have the spectrum profile of autofluorescence completely identical to that illustrated in FIGS. 30 and 31. A first modification performs image processing on the autofluorescence pattern obtained from the same kind of strain and extracts the characteristics of the pattern. Based on an original image obtained by autofluorescence (distributions of intensity data of autofluorescence), for example, the first modification extracts the characteristics by performing binarization, removal of minute objects, edge smoothing, expanded smoothing, contracted smoothing, extraction of major objects, frame extraction, branch extraction, branch masking, branch removal, minute segment removal, and other processing. The first modification thus identifies the wild strain and the mutant strain. The first modification may characterize known samples by machine learning using a plurality of autofluorescence images, for example, thereby identifying the wild strain and the mutant strain.

Figure 32A:
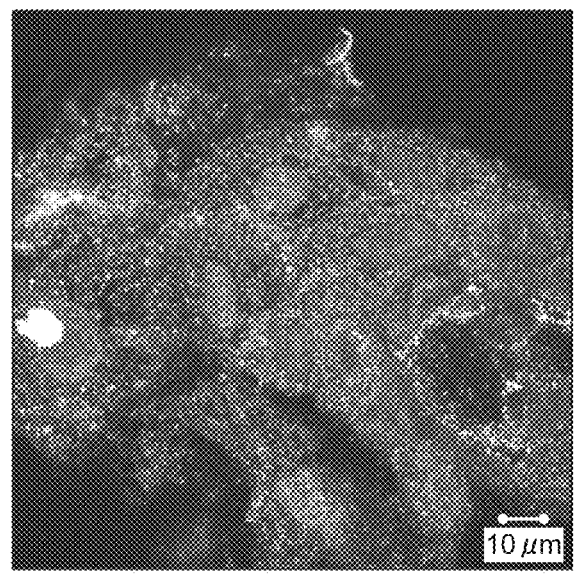
FIG. 32A is a view of a confocal reflection microscopy image of intestinal epithelial cancer cells.
Figure 32B:
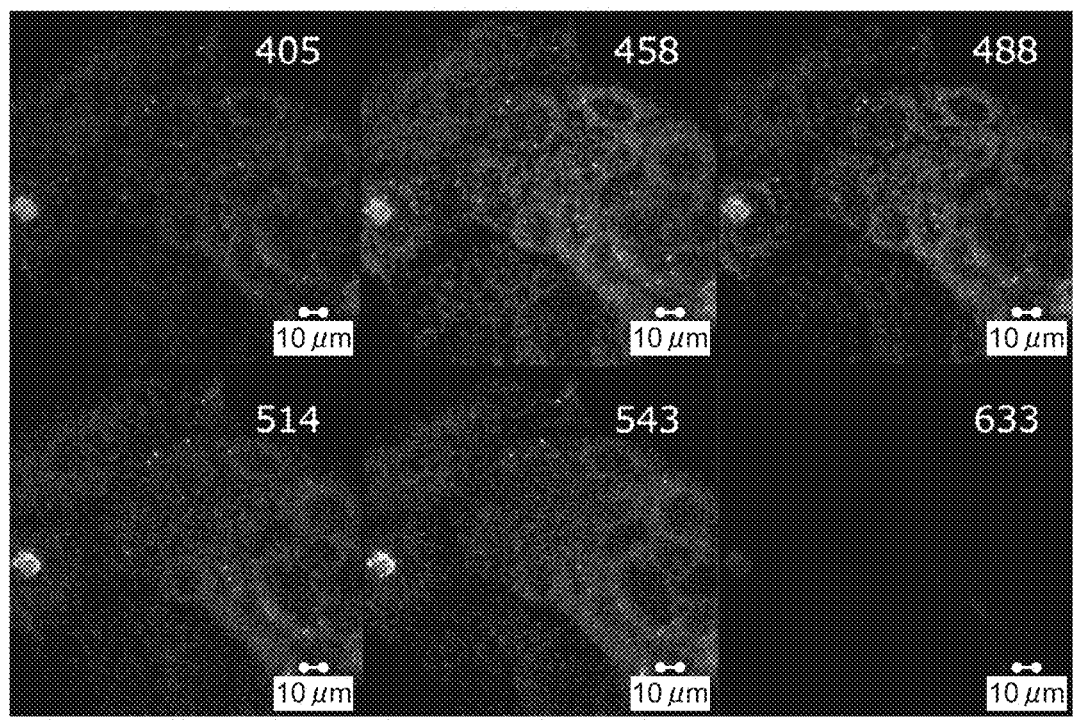
FIG. 32B is a view of autofluorescence images of the intestinal epithelial cancer cells obtained when being irradiated with respective rays of excitation light.

FIG. 32A is a view of a confocal reflection microscopy image of an intestinal epithelial cancer cell. FIG. 32B is a view of autofluorescence images of the intestinal epithelial cancer cell obtained when being irradiated with respective rays of excitation light. FIG. 32B illustrates the autofluorescence images obtained when the excitation light is output with wavelengths of 405 nm, 458 nm, 488 nm, 514 nm, 543 nm, and 633 nm. By characterizing the intestinal epithelial cancer cell illustrated in FIGS. 32A and 32B with the autofluorescence spectrum profile and the autofluorescence pattern as described above, the present embodiment can identify the intestinal epithelial cancer cell.

As described above, the embodiment according to the present invention creates the correspondence data associating the autofluorescence patterns of the specimen, the reflected light data from the specimen, and the laser light irradiation positions with one another. Based on the correspondence data, the embodiment analyzes the specimen. Consequently, the embodiment can acquire the spatial positional information on the specimen and analyze the specimen non-invasively.

The embodiment described above acquires an unknown autofluorescence pattern of the specimen, identifies the species of a microorganism by comparing the unknown autofluorescence pattern with a known autofluorescence pattern, and superimposes a hue on the position corresponding to the identified species of the microorganism in an image generated based on reflected light. Consequently, the embodiment enables visually grasping the spatial positional information on the microorganism.

Figure 33:
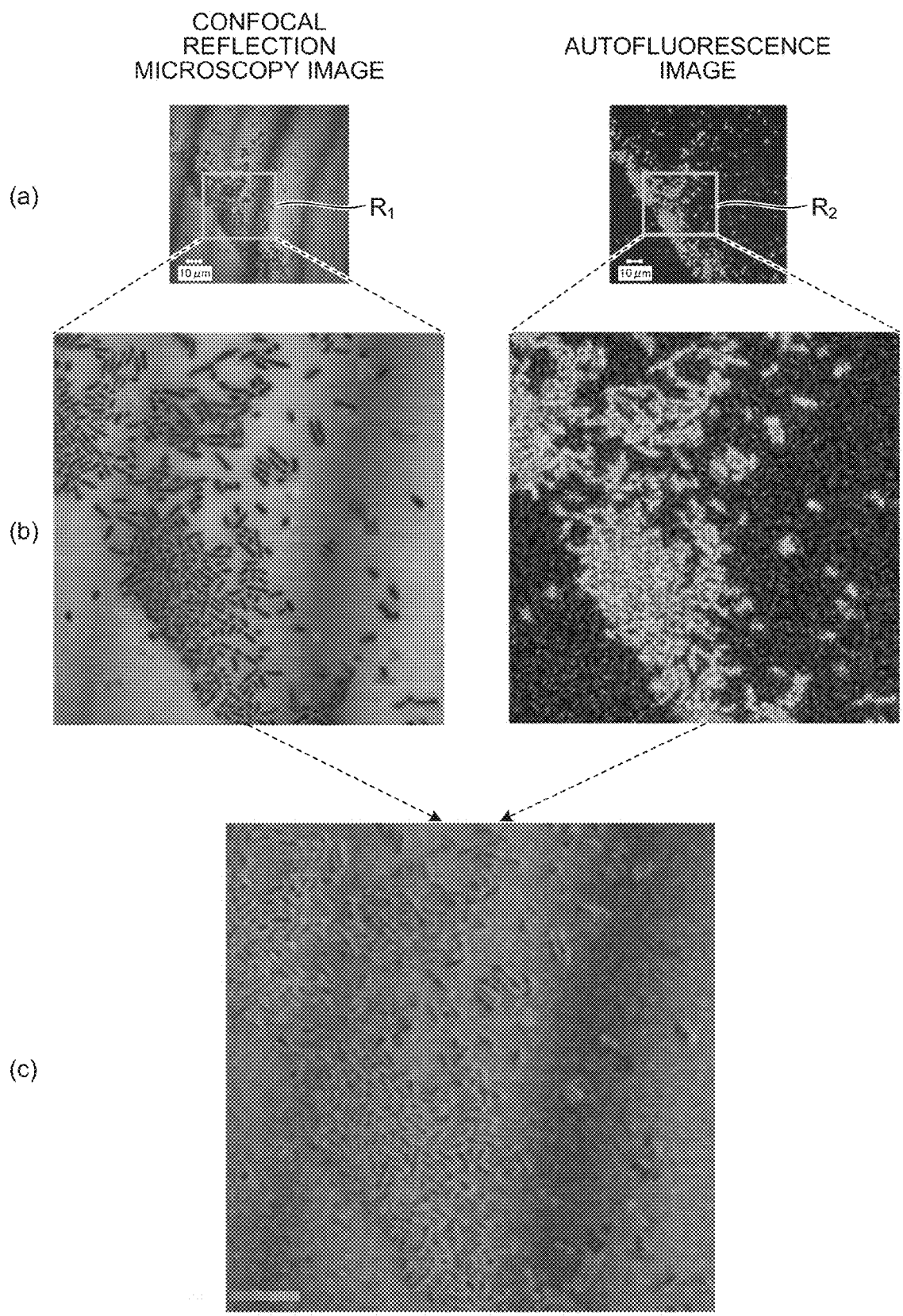
FIG. 33 is a view for explaining an image obtained by superimposing a confocal reflection microscopy image and an autofluorescence image generated by the microscopic system according to the embodiment of the present invention.

FIG. 33 is a view for explaining an image obtained by superimposing a confocal reflection microscopy image and an autofluorescence image generated by the microscopic system according to the embodiment of the present invention. FIG. 33($a$) is a view of a confocal reflection microscopy image and an autofluorescence image of *Pseudomonas putida*. The confocal reflection microscopy image and the autofluorescence image illustrated in FIG. 33($a$) has the corresponding positional relation. FIG. 33($b$) illustrates an image obtained by enlarging a region $R_1$ in the confocal reflection microscopy image illustrated in FIG. 33($a$) and an image obtained by enlarging a region $R_2$ in the autofluorescence image illustrated in FIG. 33($a$). FIG. 33($c$) illustrates an image obtained by superimposing the confocal reflection microscopy image and the autofluorescence image illustrated in FIG. 33($b$). Specifically, FIG. 33($c$) illustrates an image obtained by superimposing the autofluorescence image having predetermined transmissivity on the confocal reflection microscopy image. By superimposing and displaying the confocal reflection microscopy image and the autofluorescence image as illustrated in FIG. 33($c$), the embodiment facilitates grasping the presence position of a desired bacterium in the image and the presence regions of individual bacteria.

In the flowchart illustrated in FIG. 2, the embodiment described above obtains reflected light by light having a wavelength set in advance. If there are a plurality of rays of excitation light for obtaining autofluorescence, the embodiment may output all the rays of excitation light having different wavelengths corresponding to the rays of excitation light and obtain rays of reflected light corresponding to the respective rays of excitation light. If a plurality of rays of reflected light are obtained by the rays of excitation light, the embodiment may extract the highest intensity of the intensities of the rays of reflected light corresponding to the respective laser light irradiation positions to create the reflected light data. Alternatively, the embodiment may calculate the average of the intensities of the rays of reflected light to create the reflected light data.

First Modification

The following describes a first modification of the embodiment described above with reference to FIG. 34. Explanation of the configuration of the microscopic system according to the first modification is omitted because it is the same as the configuration of the microscopic system 1. The embodiment described above identifies the kinds and the states based on the patterns of fluorescence spectra recorded in advance. By contrast, the first modification characterizes known samples by machine learning based on the patterns of fluorescence spectra recorded in advance and specifies boundaries between the samples of different kinds or in different states. The first modification thus identifies the kind of the specimen and evaluate the state.

Figure 34:
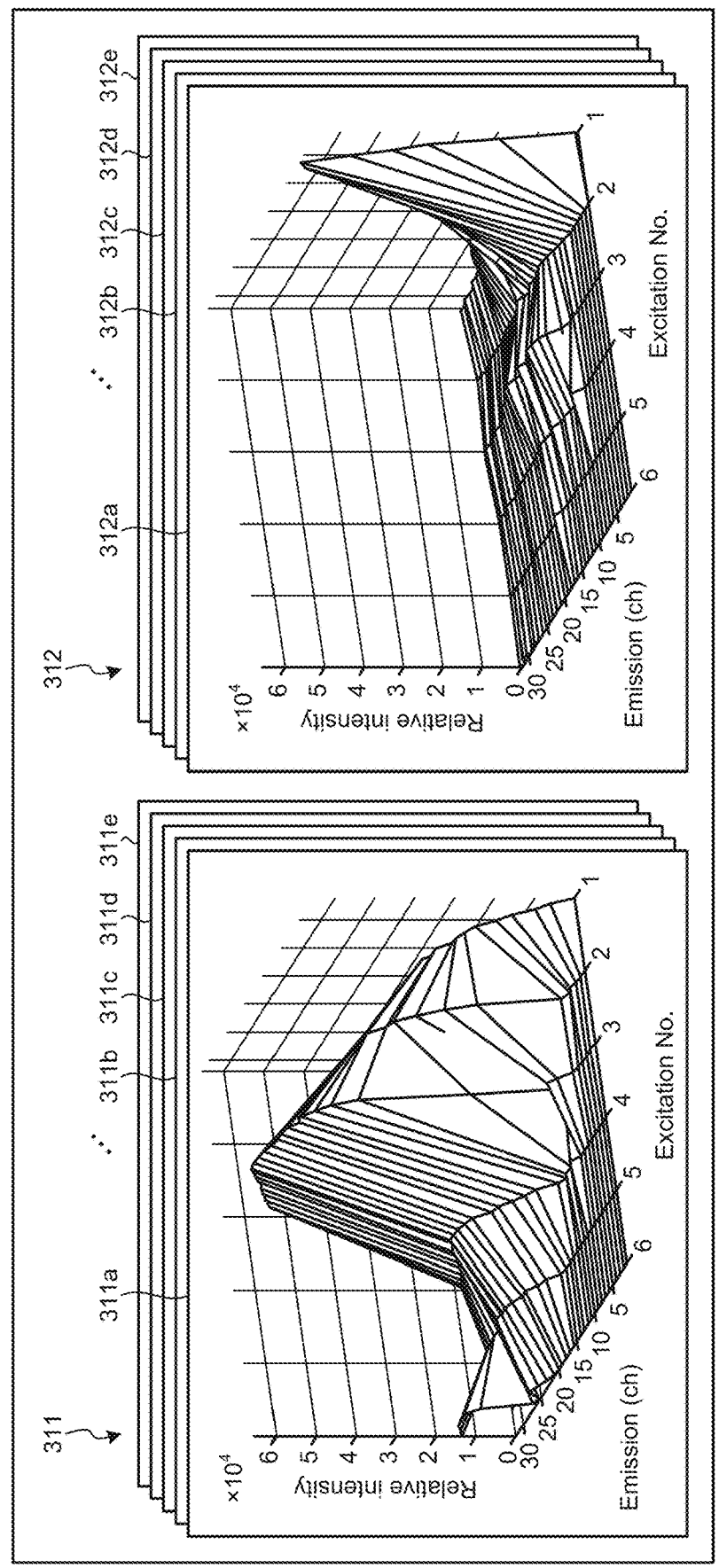
FIG. 34 is a diagram for explaining data recorded by a recorder in the microscopic system according to a first modification of the embodiment of the present invention.

FIG. 34 is a diagram for explaining data recorded by the recorder in the microscopic system according to the first modification of the embodiment of the present invention. In the first modification, as illustrated in FIG. 34, the analysis information recorder 308 records therein data sets 311 and 312 of a plurality of partially different fluorescence spectrum data as the fluorescence spectra representing a specific species. The data analyzer 305 refers to a region determined based on the data sets 311 and 312 to identify the kind and the state of the input specimen.

The data set 311, for example, includes a plurality of pieces teaching data 311$a$, 311$b$, 311$c$, 311$d$, 311$e$, . . . indicating the fluorescence intensity of autofluorescence representing a high lipid-producing strain of oleaginous yeast (Ascomycete). The pieces of teaching data 311$a$, 311$b$, 311$c$, 311$d$, 311$e$, . . . are autofluorescence intensities each representing the high lipid-producing strain and have patterns at least partially different.

The data set 312 includes a plurality of pieces teaching data 312$a$, 312$b$, 312$c$, 312$d$, 312$e$, . . . indicating the fluorescence intensity of autofluorescence representing a low lipid-accumulating strain of oleaginous yeast (Ascomycete). The pieces of teaching data 312$a$, 312$b$, 312$c$, 312$d$, 312$e$, . . . are autofluorescence intensities each representing the low lipid-accumulating strain and have patterns at least partially different.

The data analyzer 305 refers to the teaching data to extract the intensities of autofluorescence closest to the boundary dividing a region of the autofluorescence intensity representing the high lipid-producing strain and a region of the autofluorescence intensity representing the low lipid-accumulating strain, which is a boundary set in advance for the data sets 311 and 312, from the respective regions. Subsequently, the data analyzer 305 resets the boundary between the high lipid-producing strain and the low lipid-accumulating strain based on the positions of the extracted intensities in the respective regions. The reset boundary is a partial boundary divided by the wavelength of excitation light (Excitation No.) and the wavelength of autofluorescence (channel). The data analyzer 305 performs the processing described above to calculate the boundary for each pair of the wavelength of excitation light and the wavelength of autofluorescence and connects these boundaries. The data analyzer 305 thus determines the boundary between the region of the autofluorescence intensity representing the high lipid-producing strain and the region of the autofluorescence intensity representing the low lipid-accumulating strain in the three-dimensional space including the first axis, the second axis, and the third axis. If there are six rays of excitation light and 32 channels, for example, 192 partial boundaries are set and connected. Such a boundary is determined using a publicly known method, such as a support-vector machine (SVM). Alternatively, a neural network or a convolutional neural network may be established that defines a nonlinear boundary distinguishing the autofluorescence profile representing the high lipid-producing strain and the autofluorescence profile representing the low lipid-accumulating strain for the data sets 311 and 312. If there are six rays of excitation light and 32 channels, for example, a 192-dimensional vector is used as an input to a first layer of the neural network, or a matrix of 6 rows and 32 columns is used as an input to a first layer of the convolutional neural network. Such a nonlinear boundary is determined using a publicly known method, such as back-propagation and transfer learning.

Figure 35:
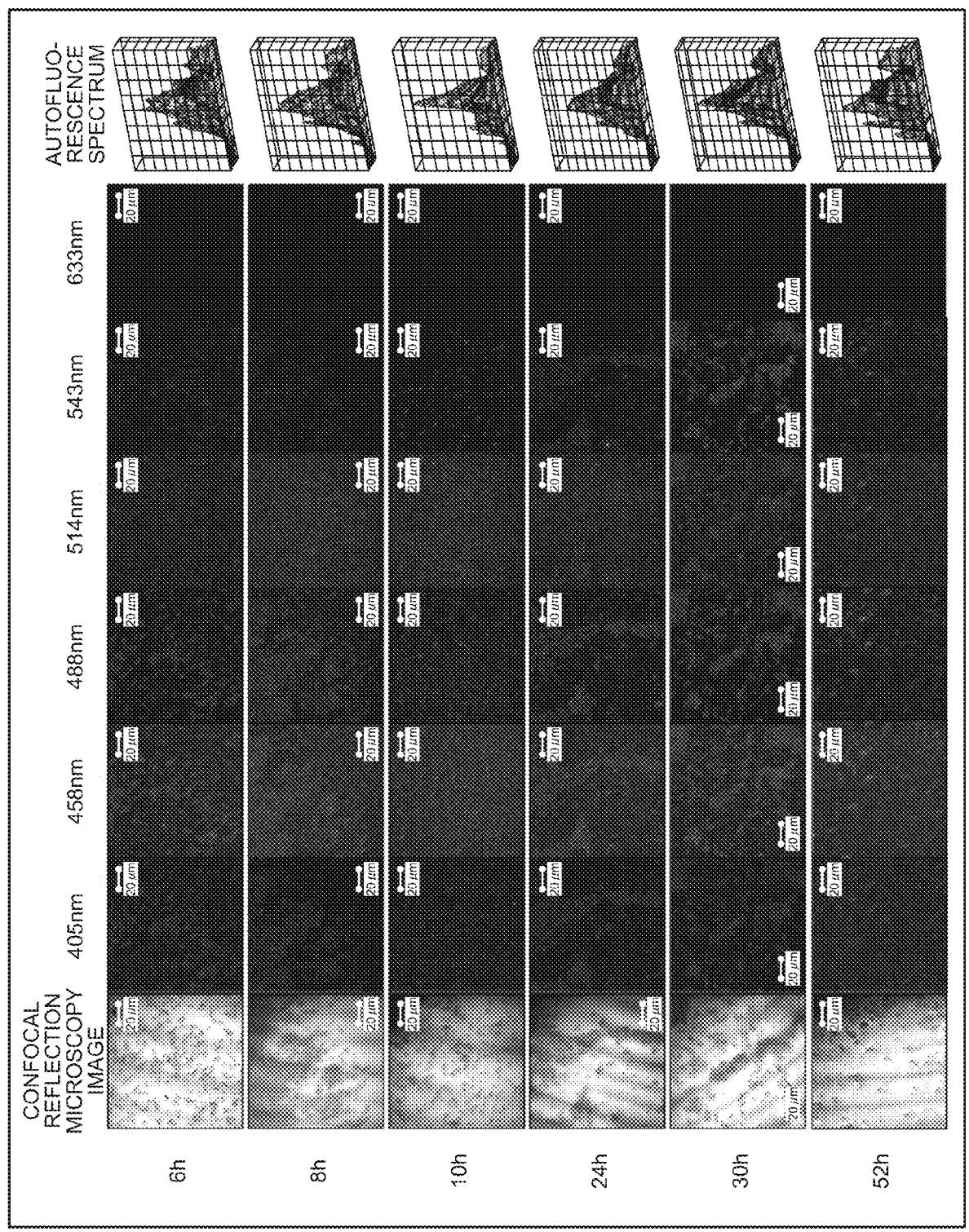
FIG. 35 is a view of confocal reflection microscopy images of *Paenibacillus polymyxa* at respective growth phases, autofluorescence images obtained when being irradiated with respective rays of excitation light, and fluorescence spectra.
Figure 36:
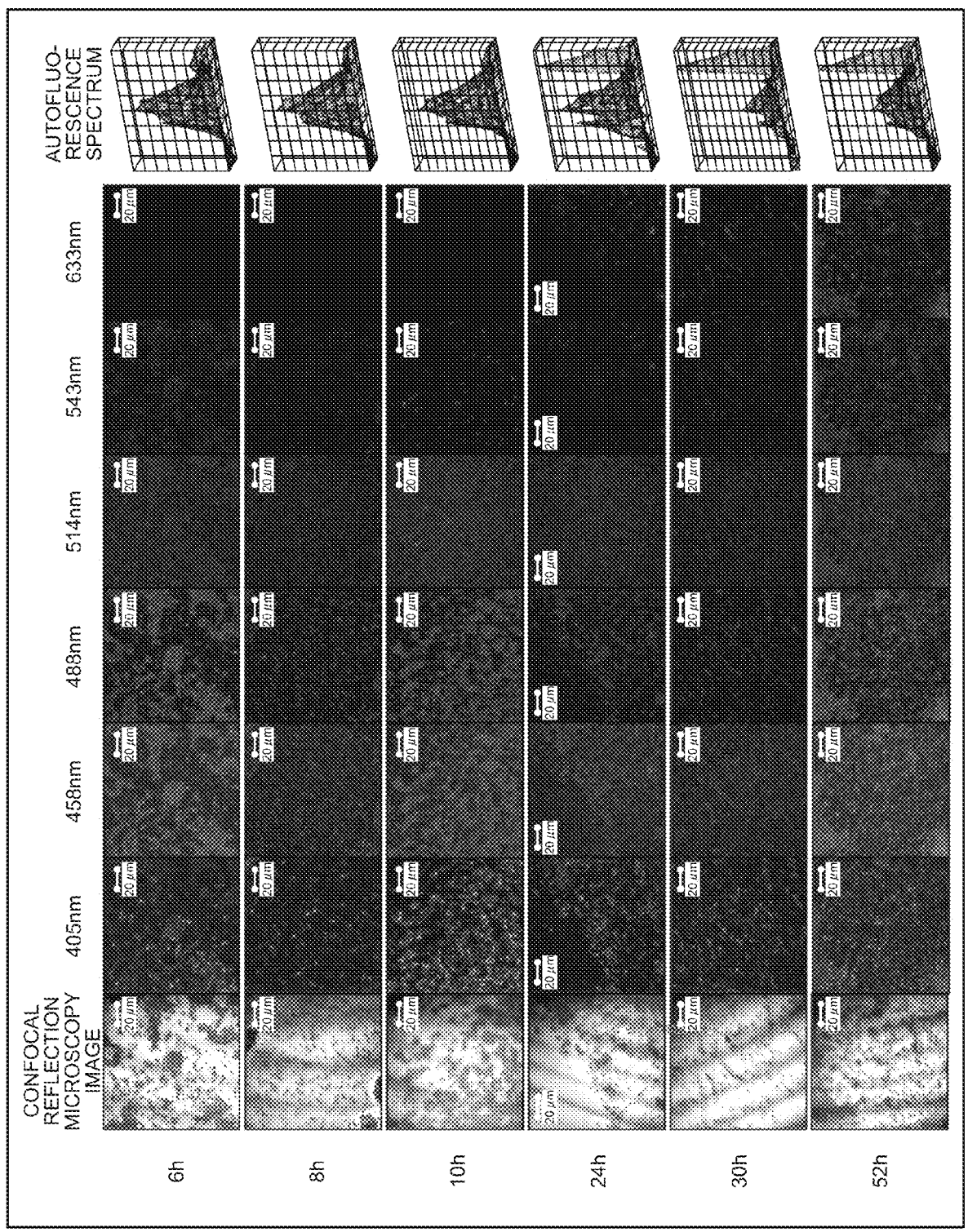
FIG. 36 is a view of confocal reflection microscopy images of *Pseudomonas putida* at respective growth phases, autofluorescence images obtained when being irradiated with respective rays of excitation light, and fluorescence spectra.

The following describes an example of determination by machine learning with reference to FIGS. 35 and 36. Cells of the same kind have different autofluorescence spectrum profiles depending on their physiological states (growth phases). FIG. 35 is a view of confocal reflection microscopy images of *Paenibacillus polymyxa* at respective growth phases, autofluorescence images obtained when being irradiated with respective rays of excitation light, and fluorescence spectra. FIG. 36 is a view of confocal reflection microscopy images of *Pseudomonas putida* at respective growth phases, autofluorescence images obtained when being irradiated with respective rays of excitation light, and fluorescence spectra. FIGS. 35 and 36 illustrate the confocal reflection microscopy images at respective growth phases of 6, 8, 10, 24, 30, and 52 hours, the autofluorescence images obtained by excitation light (wavelength: 405 nm, 458 nm, 488 nm, 514 nm, 543 nm, and 633 nm), and the autofluorescence spectrum profiles. The white lines in the respective images indicate that the length from one end to the other end of the while lines corresponds to 20 μm.

As illustrated in FIGS. 35 and 36, a single cell has different autofluorescence images and spectrum profiles of autofluorescence. By learning these spectrum profiles in a manner associated with the kinds of the cells by machine learning, the cells can be identified independently of the growth phase. As described above, the first modification performs training using the spectrum profiles of autofluorescence in various physiological states to find out the correlation of the samples. Consequently, the first modification can establish a machine learning model that can identify the cells in any physiological state. As described above, the first modification can establish the machine learning model also by performing training with the samples characterized using the autofluorescence images (distributions of intensity data of autofluorescence).

Figure 37:
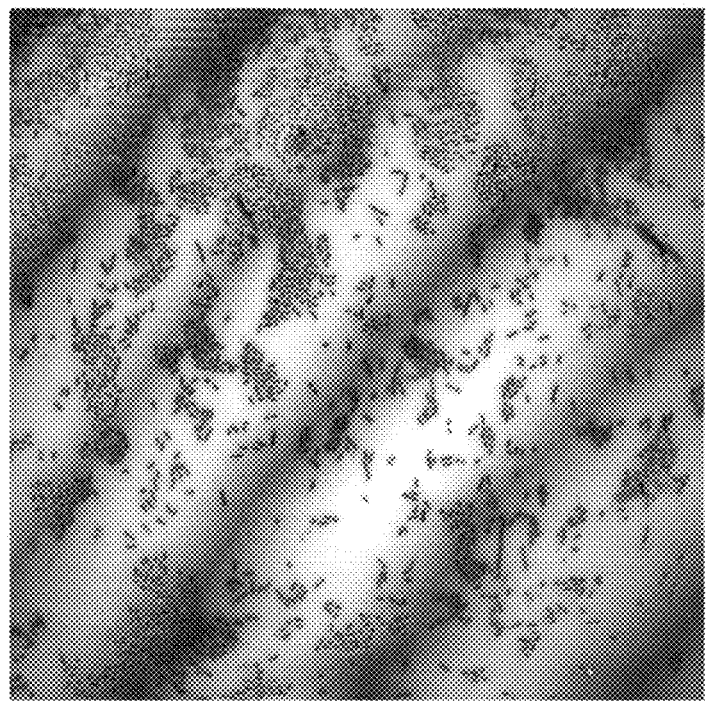
FIG. 37 is a view of a confocal reflection microscopy image in which *Paenibacillus polymyxa* and *Pseudomonas putida* are mixed.
Figure 38:
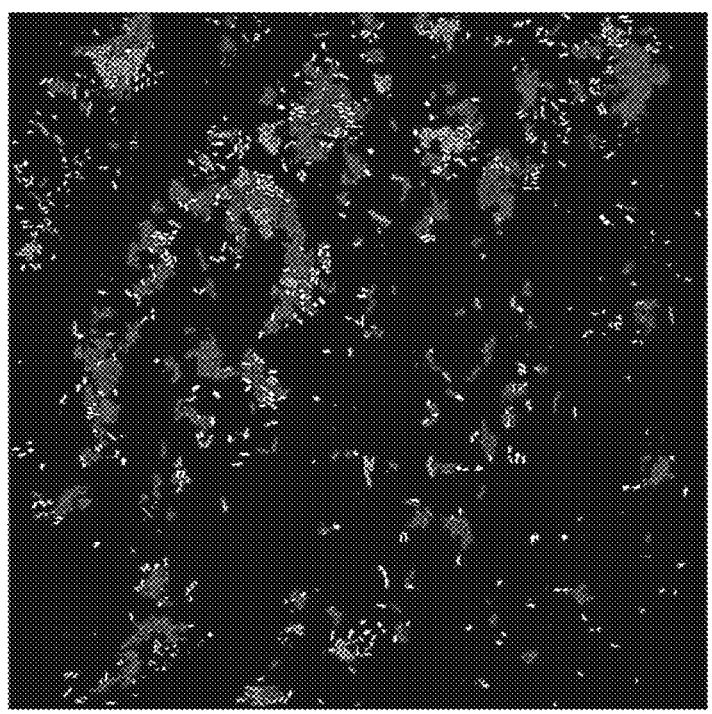
FIG. 38 is a view of an image obtained by superimposing respective hues specified for *Paenibacillus polymyxa* and *Pseudomonas putida* on the confocal reflection microscopy image.

The following describes results of identification performed by the machine learning model with reference to FIGS. 37 and 38. FIG. 37 is a view of a confocal reflection microscopy image in which *Paenibacillus polymyxa* and *Pseudomonas putida* are mixed. FIG. 38 is a view of an image obtained by superimposing respective hues specified for *Paenibacillus polymyxa* and *Pseudomonas putida* on the confocal reflection microscopy image. The image illustrated in FIG. 38 is obtained by inverting the luminance of bacteria in the confocal reflection microscopy image illustrated in FIG. 37 and coloring the background in black, and superimposing hues corresponding to the identification results. In the image illustrated in FIG. 38, *Paenibacillus polymyxa* is displayed in green, and *Pseudomonas putida* is displayed in red.

In the image (refer to FIG. 38) obtained by superimposing the hues corresponding to the result of accurate identification by machine learning on the confocal reflection microscopy image (refer to FIG. 37) in which *Paenibacillus polymyxa* and *Pseudomonas putida* are mixed, the two bacteria are distinguished by color. As described above, the first modification enables identifying the positions of the respective bacteria in the image on which the hues are superimposed.

The first modification identifies the high lipid-producing strain or the low lipid-accumulating strain based on the input fluorescence spectrum by machine learning based on the data sets 311 and 312 recorded in the analysis information recorder 308. Consequently, the first modification can identify the specimen if spectrum data having a pattern other than the patterns of the recorded fluorescence spectra.

While the first modification identifies two kinds of bacteria, it may identify three or more kinds or states. Also in this case, the first modification sets the boundaries based on the intensity distributions of autofluorescence and identify the specimen based on the input autofluorescence spectrum.

Second Modification

The following describes a second modification of the embodiment described above with reference to FIG. 39. Explanation of the configuration of the microscopic system according to the second modification is omitted because it is the same as the configuration of the microscopic system 1. The embodiment described above scans the whole scanning region to obtain the autofluorescence data. By contrast, the second modification specifies a position from which autofluorescence is to be obtained based on the reflected light data and outputs excitation light only to the specified position.

Figure 39:
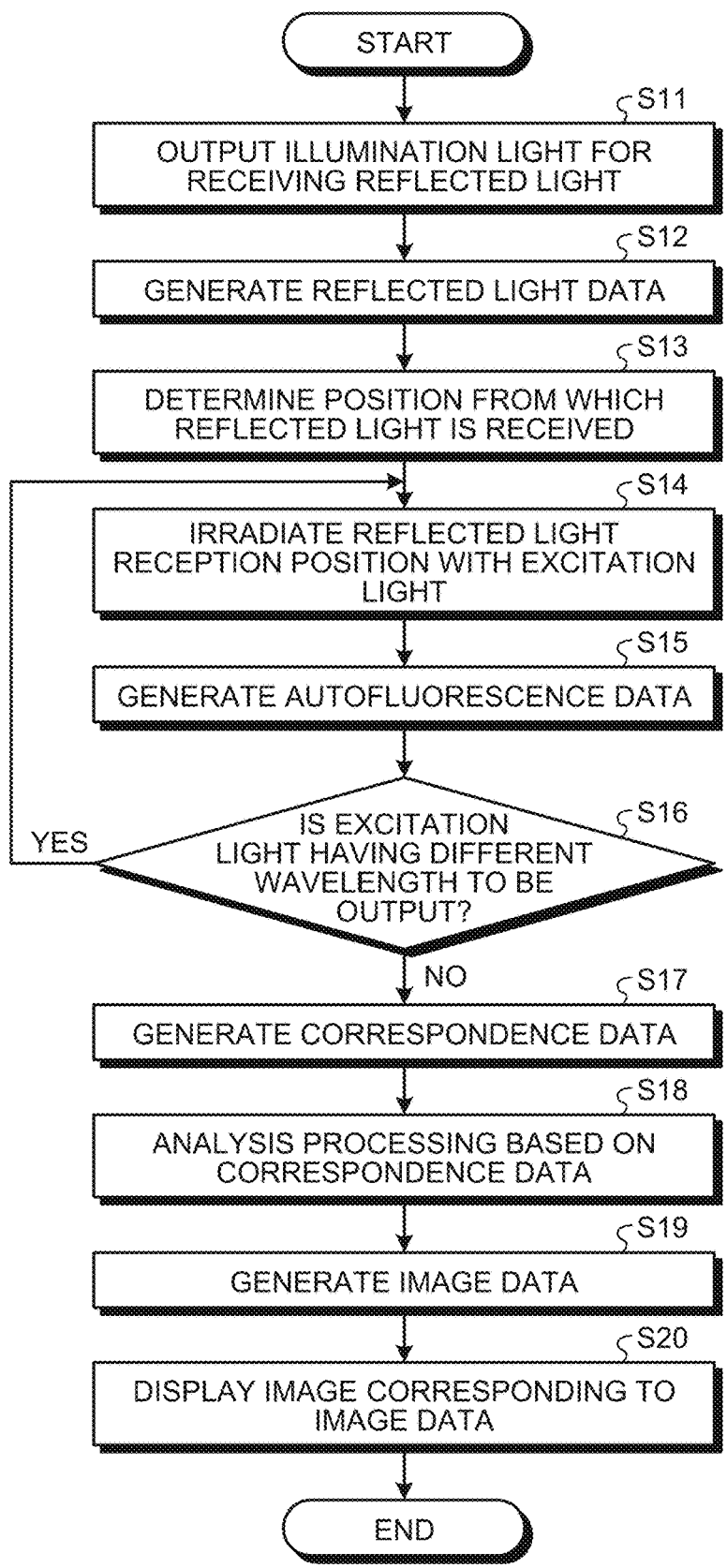
FIG. 39 is a flowchart for explaining a data analysis method according to a second modification of the embodiment of the present invention.

FIG. 39 is a flowchart for explaining the data analysis method according to the second modification of the embodiment of the present invention. The following describes a process of analyzing a specimen and generating the superimposition image data based on the obtained autofluorescence.

In the image generation method according to the second modification, the microscopic system irradiates a specimen with illumination light (preferably, laser light) for obtaining reflected light under the control by the controller 201 (Step S11). The detection signal receiver 301 obtains reflected light generated by the illumination light. The illumination light used at Step S11 is light for obtaining reflected light reflected by the specimen. The illumination light may be light having a specific wavelength band, such as excitation light for obtaining autofluorescence, or white light. At Step S11, the microscopic system scans the whole scanning region.

At Step S12 subsequent to Step S11, the reflected light data generator 302b acquires detection signals relating to the reflected light received by the detection signal receiver 301 and generates reflected light data based on the acquired detection signals (reflected light data generation step).

At Step S13 subsequent to Step S12, the data analyzer 305 refers to the reflected light data to determine the position from which the reflected light is received, that is, the position at which the specimen is present. The data analyzer 305, for example, determines a position from which an intensity equal to or higher than a threshold set in advance is acquired to be a specimen presence position. The set threshold is a value larger than the intensity determined to be noise, for example.

At Step S14 subsequent to Step S13, the microscopic system irradiates the position at which the specimen is determined to be present with excitation light (preferably, laser light) under the control by the controller 201. The detection signal receiver 301 obtains autofluorescence generated by the excitation light.

Subsequently, the autofluorescence data generator 302a acquires detection signals relating to the autofluorescence received by the detection signal receiver 301 and generates autofluorescence data based on the acquired detection signals (Step S15: autofluorescence data generation step). In the autofluorescence data, the fluorescence spectrum is supplied only to the position at which the specimen is determined to be present at Step S13. In other words, the autofluorescence data is thinning data when the acquired fluorescence spectra are aligned corresponding to the scanning position.

At Step S16 subsequent to Step S15, the controller 201 determines whether to output excitation light having a wavelength (or wavelength band) different from the wavelength (or wavelength band) of the excitation light output at Step S14. The controller 201 refers to scanning conditions set in advance or scanning conditions specified through the input unit 202 to determine whether another excitation light to be output is present. If the controller 201 determines that excitation light having a wavelength different from that of the light output at Step S14 needs to be output (Yes at Step S16), the microscopic system performs the processing at Step S14 again to repeat scanning using the excitation light at the position where the specimen is determined to be present. If the controller 201 determines that another excitation light need not be output (No at Step S16), the microscopic system performs the processing at Step S17.

At Step S17, the correspondence data generator 302c generates correspondence data associating the intensity of reflected light generated at Step S12 and the fluorescence spectrum generated at Step S15 with the laser light irradiation position (correspondence data creation step).

At Step S18 subsequent to Step S17, the data analyzer 305 performs analysis processing on the specimen based on the correspondence data generated at Step S17. At Step S18, for example, similarly to the embodiment described above, the data analyzer 305 identifies the kind of a microorganism at an autofluorescence obtaining position (specimen presence position).

At Step S19 subsequent to Step S18, the two-dimensional image generator 303, the three-dimensional image generator 304, and the hue superimposer 306 generate image data based on the correspondence data. At Step S19, the two-dimensional image generator 303 generates a plurality of pieces of focused image data first using the reflected light data in the correspondence data.

At Step S20 subsequent to Step S19, the image processing device 300 causes the display device 400 to display the superimposition image data generated by the hue superimposer 306 under the control by the control device 200. By the processing described above, the display device 400 displays a superimposition image obtained by coloring the specimen image generated by irradiation of the excitation light based on the analysis results (kinds).

The second modification can provide the same advantageous effects as those of the embodiment described above. In addition, the second modification requires a shorter scanning time for obtaining autofluorescence and a smaller amount of data than the embodiment described above because it narrows down the position from which the autofluorescence is obtained from the reflected light data.

Some cells contain an air bubble or a vacuole inside thereof. The illumination light fails to be reflected at the position (coordinates) of the air bubble or the vacuole, whereby no reflected light may possibly be obtained. To address this, the second modification may obtain the autofluorescence by irradiating not only the specimen presence position determined based on the reflected light data but also the whole inner region of the specimen detected based on the specimen presence position with the excitation light. The second modification, for example, irradiates a plurality of positions where the specimen is determined to be present, that is, a plurality of sets of coordinates, and all the coordinates in the region surrounded by the sets of coordinates with the exciting light, thereby obtaining the autofluorescence at the sets of coordinates. Consequently, if the specimen, such as a cell, has a part from which no reflected light is obtained due to an air bubble or a vacuole, the second modification can obtain the autofluorescence by irradiating the entire cell (in particular, the part from which no reflected light is obtained due to an air bubble, a vacuole, or the like) with the excitation light.

Besides the processing according to the embodiment described above and the modifications thereof, the data analyzer 305, for example, may extract a specimen having predetermined properties from an unknown sample. Specifically, at Step S6 in FIG. 2, the data analyzer 305 extracts a specimen that emits autofluorescence having a predetermined wavelength or a specimen having a predetermined fluorescence spectrum due to a predetermined excitation wavelength (extraction step). At Step S7, the microscopic system 1 may image the information generated by the extraction processing. Specifically, the microscopic system 1 may superimpose hues on the extracted part, for example, in the reflected light image and display the image resulting from superimposition. Alternatively, the microscopic system 1 may end the processing without performing the processing at Steps S7 and S8 after generating the extraction information.

While the aspects to embody the present invention have been described, the embodiment described above is not intended to limit the present invention. While the embodiment described above generates a fluorescence spectrum based on autofluorescence emitted from a microorganism in a specimen and identifies the kind of the microorganism, the object to be identified is not limited to the species of microorganisms. The present invention can be applied to organisms, such as separated cells, having specific fluorescence spectra due to irradiation of laser light.

The embodiment described above scans a three-dimensional space, thereby generating the autofluorescence data, the reflected light data, and the correspondence data. Alternatively, the embodiment may scan a two-dimensional space (any one of the X-Y plane, the X-Z plane, and the Y-Z plane illustrated in FIG. 3), thereby generating the autofluorescence data, the reflected light data, and the correspondence data. Still alternatively, the embodiment may perform scanning in any one of the X-direction, the Y-direction, and the Z-direction illustrated in FIG. 3 or obtain autofluorescence and reflected light of one point in a space, thereby generating the autofluorescence data, the reflected light data, and the correspondence data.

The embodiment described above generates and displays a three-dimensional image. Alternatively, the embodiment may display a two-dimensional image or superimpose visual information. Still alternatively, the embodiment may select an image to be displayed by an operating input from a user.

The embodiment described above generates a two-dimensional image and a three-dimensional image based on the reflected light reflected by the specimen. In addition, the embodiment may generate a two-dimensional image and a three-dimensional image by a publicly known method including a method for visualization by a specific wavelength or visible light, such as stereoscopic visualization by confocal reflection microscopy, two-dimensional visualization by differential interferometry, and two-dimensional visualization by transmitted light.

The detector 109 according to the embodiment described above is provided as a reflective diffraction grating and photomultiplier tubes (PMTs). In addition, the detector 109 may be provided as an acousto-optic beam splitter (e.g., AOBS (registered trademark) manufactured by Leica camera AG), a highly sensitive detector (HyD detector), or a detector including a movable slit structure provided in a stage preceding the detector. With the configuration described above, the detector can acquire data divided in units of a wavelength of 1 nm, for example.

While the embodiment described above superimposes specified hues on an image, the object to be superimposed is not limited to the hues. The present invention can be applied to visually recognizable objects, such as shading.

While the embodiment described above obtains reflected light or autofluorescence using laser light, the object to be output is not limited to light having high directivity, such as laser light. The embodiment may condense light having low directivity (e.g., light output by a halogen lamp) and irradiates a sample with the condensed light, thereby obtaining reflected light or autofluorescence. The embodiment, for example, may obtain autofluorescence by laser light and obtain reflected light using a halogen lamp. Alternatively, the embodiment may obtain autofluorescence using a halogen lamp and obtain reflected light by laser light. Still alternatively, the embodiment may obtain autofluorescence and reflected light using a halogen lamp. The wavelength of light may be a wavelength of light passing through a filer or separated by a prism.

The embodiment described above identifies a kind using fluorescence spectra corresponding to a plurality of excitation wavelengths. If identification is enabled, the embodiment may identify a kind using a fluorescence spectrum corresponding to one excitation wavelength. The embodiment described above performs the analysis by comparing the peak position of the obtained fluorescence spectrum with that of the known fluorescence spectrum. The embodiment may perform the analysis using the intensity of the peak or the intensity ratio of the peak, for example. In the analysis using the intensity, the autofluorescence data is data associating the intensity of detected autofluorescence with the position and the excitation wavelength.

As described above, the present invention can include various embodiments without departing from the technical idea described in the claims.

INDUSTRIAL APPLICABILITY

As described above, the data creation method and the data use method according to the present invention can analyze a sample non-invasively and acquire spatial positional information on the object.

REFERENCE SIGNS LIST 1 microscopic system
100 confocal laser scanning microscope
101 stage
102 object lens
103 laser light source
104 lens
105 collimating lens
106 beam splitter
107 imaging lens
108 confocal pinhole
109 detector
110 scanning mirror
200 control device
201 controller
202 input unit
203 laser controller
204 scanning controller
300 image processing device
301 detection signal receiver
302 data generator
302a autofluorescence data generator
302b reflected light data generator
302c correspondence data generator
303 two-dimensional image generator
304 three-dimensional image generator
305 data analyzer
306 hue superimposer
307 recorder
308 analysis information recorder
400 display device

The invention claimed is:

1. A data creation method comprising:
an autofluorescence data generation step of placing a focus of excitation light having a predetermined wavelength at one set of coordinates on a predetermined focal plane, irradiating a sample positioned at the set of coordinates with the excitation light to obtain autofluorescence emitted from the sample, and generating autofluorescence data including intensity data and/or spectrum data of the autofluorescence;
a reflected light data generation step of irradiating the set of coordinates on the predetermined focal plane with illumination light to obtain reflected light scattered by the sample, and generating intensity data of the reflected light; and
a correspondence data creation step of creating correspondence data associating the autofluorescence data and the intensity data of the reflected light on the set of coordinates on the predetermined focal plane,
wherein the data creation method is performed on a plurality of different sets of coordinates on the predetermined focal plane.

2. The data creation method according to claim 1, wherein the data creation method is performed on a plurality of different focal planes.

3. The data creation method according to claim 1, wherein the autofluorescence data generation step includes outputting a plurality of rays of excitation light having different wavelengths and creating the autofluorescence data including spectrum profile data containing a plurality of pieces of the spectrum data of the autofluorescence obtained by the respective rays of excitation light.

4. The data creation method according to claim 3, wherein the reflected light data generation step includes obtaining the reflected light using any one of the rays of excitation light having different wavelengths.

5. The data creation method according to claim 3, wherein the reflected light data generation step includes obtaining the reflected light using all the rays of excitation light having different wavelengths.

6. The data creation method according to claim 1, wherein the autofluorescence data generation step is performed only on a set of coordinates from which the reflected light having an intensity equal to or higher than a predetermined intensity is obtained at the reflected light data generation step.

7. The data creation method according to claim 1, wherein the autofluorescence data generation step is performed on a plurality of sets of coordinates from which the reflected light having an intensity equal to or higher than a predetermined intensity is obtained at the reflected light data generation step and on one or a plurality of sets of coordinates positioned in a region that is surrounded by the sets of coordinates and that corresponds to an inside of the sample.

8. The data creation method according to claim 1, wherein at least one of the excitation light and the illumination light is laser light.

9. A data use method comprising generating the correspondence data by the data creation method according to claim 1 and finding out correlation with a state of a sample by comparing a plurality of pieces of the autofluorescence data of the sample.

10. The data use method according to claim 9, wherein the correlation is found out by machine learning.

11. The data use method according to claim 9, wherein the sample is any one of an animal cell, a plant cell, an yeast cell, an eumycetes cell, a microalgae cell, a bacterium, an archaeon, a virus, and a phage and any one of a spore, a sporule, and a membrane vesicle produced by the cells and the organisms.

12. The data use method according to claim 9, wherein the state of the sample relates to a metabolic state or a physiological state of the sample.

13. A data use method comprising generating the correspondence data by the data creation method according to claim 1 and identifying or evaluating an unknown sample by comparing the autofluorescence data of a known sample with the autofluorescence data of the unknown sample.

14. The data use method according to claim 13, wherein the known sample is characterized by machine learning.

15. The data use method according to claim 13, wherein identification of the unknown sample is to identify a biological kingdom, phylum, class, order, family, genus, species, breed, pathotype or serotype.

16. The data use method according to claim 13, wherein identification of the unknown sample is to identify a microbiological strain or sub-strain.

17. The data use method according to claim 13, wherein evaluation of the unknown sample relates to a metabolic state or a physiological state.

18. The data use method according to claim 13, wherein the sample is any one of an animal cell, a plant cell, an yeast cell, an eumycetes cell, a microalgae cell, a bacterium, an archaeon, a virus, and a phage and any one of a spore, a sporule, and a membrane vesicle produced by the cells and the organisms.

19. A data use method comprising:
an autofluorescence data generation step of placing a focus of light having a predetermined wavelength at one set of coordinates on a predetermined focal plane, irradiating a sample positioned at the set of coordinates with excitation light containing the light to obtain autofluorescence emitted from the sample, and generating autofluorescence data including intensity data and/or spectrum data of the autofluorescence;
a reflected light data generation step of irradiating the set of coordinates on the predetermined focal plane with illumination light to obtain reflected light scattered by the sample, and generating intensity data of the reflected light;
a correspondence data creation step of creating correspondence data associating the autofluorescence data and the intensity data of the reflected light on the set of coordinates on the predetermined focal plane;
a repetition step of repeating the autofluorescence data generation step, the reflected light data generation step, and the correspondence data creation step on a plurality of different focal planes; and
an extraction step of extracting a group having a predetermined property using the correspondence data obtained by the repetition step.

* * * * *